(12) United States Patent
Henschke et al.

(10) Patent No.: US 8,846,953 B2
(45) Date of Patent: Sep. 30, 2014

(54) PROCESSES FOR THE PREPARATION OF 3-(PYRROL-2-YL)METHYLENE)-2-PYRROLONES USING 2-SILYLOXY-PYRROLES

(75) Inventors: Julian P. Henschke, Tainan (TW); Yung-Fa Chen, Tainan (TW)

(73) Assignee: Scinopharm Taiwan, Ltd., Tainan (TW)

( * ) Notice: Subject to any disclaimer, the term of this patent is extended or adjusted under 35 U.S.C. 154(b) by 0 days.

(21) Appl. No.: 13/878,693

(22) PCT Filed: Nov. 1, 2010

(86) PCT No.: PCT/CN2010/001731
§ 371 (c)(1),
(2), (4) Date: Apr. 10, 2013

(87) PCT Pub. No.: WO2012/058780
PCT Pub. Date: May 10, 2012

(65) Prior Publication Data
US 2013/0190512 A1    Jul. 25, 2013

(51) Int. Cl.
*C07D 403/06*    (2006.01)
(52) U.S. Cl.
CPC .................................. *C07D 403/06* (2013.01)
USPC ........................... 548/468; 548/518; 548/455
(58) Field of Classification Search
None
See application file for complete search history.

(56) References Cited

U.S. PATENT DOCUMENTS

| | | |
|---|---|---|
| 2003/0229229 A1 | 12/2003 | Jin et al. |
| 2005/0059824 A1* | 3/2005 | Vaidyanathan et al. ........ 544/59 |
| 2005/0090541 A1 | 4/2005 | Arnaiz et al. |
| 2006/0009510 A1 | 1/2006 | Havens et al. |
| 2009/0062368 A1 | 3/2009 | Czarnik |
| 2009/0247767 A1 | 10/2009 | Bigatti et al. |
| 2009/0318525 A1 | 12/2009 | Mangion et al. |
| 2011/0306647 A1* | 12/2011 | Parthasaradhi Reddy et al. .............................. 514/414 |
| 2012/0029046 A1* | 2/2012 | Gore et al. ..................... 514/414 |

FOREIGN PATENT DOCUMENTS

| | | |
|---|---|---|
| CN | 101333215 A | 12/2008 |
| CN | 101497607 A | 8/2009 |
| WO | 0160814 A2 | 8/2001 |
| WO | 2005058309 A1 | 6/2005 |
| WO | 2008067756 A1 | 6/2008 |
| WO | 2009030270 A1 | 3/2009 |
| WO | 2009124037 A1 | 10/2009 |
| WO | 2010001167 A2 | 1/2010 |

OTHER PUBLICATIONS

Sun et al., Bioorganic & Medicinal Chemistry Letters, 2002, 12, 2153-2157.
Krystal et al., Cancer Research 2001, 61, 3660-3668.
Ma et al., Journal of Investigative Dermatology 2000, 114, 392-394.
Islam et al., Bioorganic & Medicinal Chemistry Letters 17 (2007) 3814-3818.
Islam et al., Bioorganic & Medicinal Chemistry Letters 2007, 17, 3819-3825.
Manley et al., J. Org. Chem. 2003, 68, 6447-6450.
Bollyn, Organic Process Research & Development 2005, 9, 982-996.
Sun et al., J. Med. Chem. 2003, 46, 1116-1119.
Vorbrüggen H. et al., "Handbook of Nucleoside Synthesis", John Wiley & Sons, Inc., 2001, ISBN 0-471-09383-1, pp. 10-47, 54-55, and 90-101.
McIntyre et al, Drugs of the Future 2005, 30(8): 785-792.
Boue'rat et al, J. Med. Chem. 2005, 48, 5412-5414.
Extended European Search Report issued on Mar. 24, 2014 for the European counterpart application No. 10859128.0.
First Examination Report issued on Jan. 22, 2014 for the New Zealand counterpart application No. 609475.

* cited by examiner

*Primary Examiner* — Nyeemah A Grazier
(74) *Attorney, Agent, or Firm* — Enshan Hong; Kent H. Cheng; VLP Law Group LLP

(57) ABSTRACT

The present invention provides for synthetic processes for the making of substituted 3-((pyrrol-2-yl)methylene)-2-pyrrolones, including sunitinib. The present invention also provides for a process of crystallizing substantially pure sunitinib L-malate.

21 Claims, 5 Drawing Sheets 3-((Pyrrol-2-yl)methylene)-2-pyrrolones   3-((pyrrol-2-yl)methylene)-2-indolinones

PROCESSES FOR THE PREPARATION OF 3-(PYRROL-2-YL)METHYLENE)-2-PYRROLONES USING 2-SILYLOXY-PYRROLES

RELATED APPLICATIONS

This is a U.S. national stage of application No. PCT/CN2010/001731, filed on Nov. 1, 2010, the content of which is incorporated here by reference.

BACKGROUND OF THE INVENTION

1. Field of the Invention

The present invention provides for synthetic processes for the making of substituted 3-((pyrrol-2-yl)methylene)-2-pyrrolones, including sunitinib.

2. Description of the Related Art 3-((Pyrrol-2-yl)methylene)-2-pyrrolones (3; FIG. 1) occur as core structural units in a significant number of reported chemical structures[1], many of which have been synthesised for biological testing for their potential use as drugs. Typically the 2-pyrrolone sub-unit manifests itself as a substituted or unsubstituted 2-indolinone (i.e., 3-((pyrrol-2-yl)methylene)-2-indolinones 3b), or as a 2-pyrrolone fused with a heterocyclic aromatic ring. For convenience we will class 3-((pyrrol-2-yl)methylene)-2-indolinones 3b as 3-((pyrrol-2-yl)methylene)-2-pyrrolones 3. The methylene group that bridges the pyrrolone and pyrrole rings can be partially substituted (i.e., $R^5$=H) or fully substituted (e.g., $R^5$=alkyl, aryl, COR). As such, the 3-((pyrrol-2-yl)methylene-2-pyrrolone moiety can be found in biologically active compounds being investigated for the treatment of, or have been suggested to have the potential for treating, a range of diseases including cancer,[2] inflammation, a range of autoimmune diseases (including rheumatoid arthritis and multiple sclerosis[3]), Parkinson's disease,[4] and cardiovascular disease. Examination of the literature revealed that the 3-((pyrrol-2-yl)methylene)-2-pyrrolone moiety seen in biologically active compounds modulates the activity of protein kinases. Protein kinases are critical regulators of cellular processes in normal tissues and in diseased tissue, including cancer. Thus, the efficient synthesis of this structural moiety is of significant relevance to the identification, development and manufacture of new drugs to treat disease.

[1]As confirmed using a SciFinder search on this molecular moiety (24 Apr. 2010).
[2]*Bioorganic & Medicinal Chemistry Letters*, 2002, 12, 2153-2157.
[3]WO2005058309A1; Medicinal Chemistry, 2005, 48, 5412-5414.
[4]WO2009030270A1.

One particular example of a clinically useful 3-((pyrrol-2-yl)methylene)-2-pyrrolone is N-[2-(diethylamino)ethyl]-5-[(Z)-(5-fluoro-1,2-dihydro-2-oxo-3H-indol-3-yliden)methyl]2,4-dimethyl-1H-pyrrole-3-carboxamide) ($C_{22}H_{27}FN_4O_2$; MW 398.47 g/mol), otherwise known as sunitinib (1) which is used as its L-malic acid ((2S)-hydroxybutanedioic acid) salt 2[5] as the active pharmaceutical ingredient in SUTENT® (FIG. 2). SUTENT®, previously known as SU11248, is marketed by Pfizer Inc. The active ingredient is a first-in-class orally available, small molecule receptor tyrosine kinase (RTK) inhibitor which is used for the treatment of gastrointestinal stromal tumor (GIST) and renal cell carcinoma (RCC). Sunitinib and/or its salt is/are also being evaluated in a broad range of solid tumors, including breast, lung, thyroid and colorectal cancers.

[5]$C_{26}H_{33}FN_4O_7$, and a MW of 532.6 (g/mol).

Other biologically active compounds of interest that possess the 3-((pyrrol-2-yl)methylene)-2-pyrrolone moiety include those shown in FIG. 3. Compounds such as SU5416 and SU6597 have been studied for the possible use in the inhibition of the proliferation of tumors ("such as SCLC, gastrointestinal stromal tumors, seminomas, and leukemias."[6]) and SU6577 for a "therapy targeting a cause of mastocytosis"[7], and PHA665752 for antitumor activity, and A-432411 as a microtubule inhibitor, and BX-517[8] for cancer.

[6]*Cancer Research* 2001, 61, 3660-3668.
[7]*Journal of Investigative Dermatology* 2000, 114, 392-394.
[8]*Bioorganic & Medicinal Chemistry Letters*, 2002, 12, 2153-2157.

3-((Aryl)methylene)-2-pyrrolones such as SU4984 might also be useful for disease therapies, and these analogues of 3-((pyrrol-2-yl)methylene)-2-pyrrolones might be applicable to synthesis using the processes described in this invention.

SUMMARY OF THE INVENTION

Part 1: A Summary of the Prior Art 3-((Pyrrol-2-yl)methylene)-2-pyrrolones 3 are usually synthesised by the base catalysed coupling of 2-pyrrolones 4 and 2-formyl-pyrroles 5a (Scheme 1). The coupling is analogous to the Knoevenagel condensation from which olefins rather than aldol products (i.e., β-hydroxy-carbonyl compounds) are obtained. No other methods have been reported to our knowledge besides one described in Scheme 9 and a $TiCl_4$ catalysed version in which the 2-formyl-pyrrole is replaced with a 2-acyl-pyrrole 5b. Bases used in the coupling reaction include secondary (e.g., piperidine and pyrrolidine) or tertiary amines (e.g., $Et_3N$ and DIPEA), alkaline metal alkoxides (e.g., KOH) or carbonates (e.g., $K_2CO_3$) which are used in substoichiometric, stoichiometric or greater than stoichiometric amounts. Solvents typically include polar protic and aprotic solvents such as alcohols (e.g., EtOH) and DMF. The reactions are typically conducted in the presence of a catalytic amount of base with heating at moderate temperatures. The yields vary from less than 50% to high.

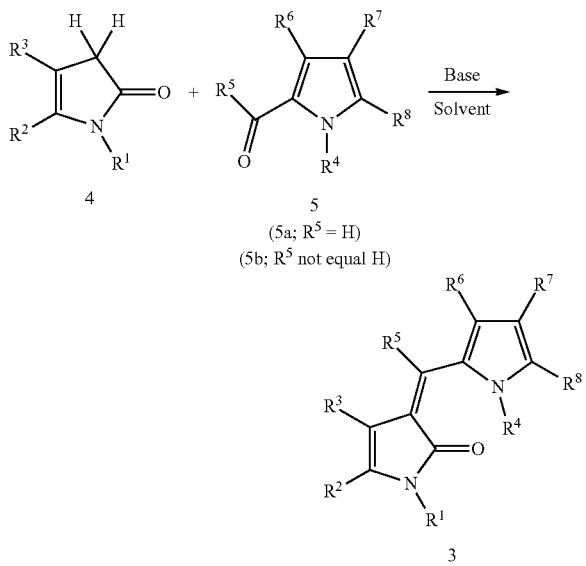

Scheme 1-Synthesis of 3-((pyrrol-2-yl)methylene)-2-pyrrolones

When $R^5$ is not a hydrogen (i.e., $COR^5$ is not an aldehyde functional group), the couplings typically must be conducted under considerably more harsh conditions[9] such as in DMF at >100° C. for several days or using microwave irradiation, or even in a sealed tube without solvents.[10] Yields are generally low at typically around 50%, or less. In some examples (5b; where $R^5 \neq H$) harsh conditions ($\geq 100°$ C.) in the presence of >1 molar equivalent (w.r.t. 2-acyl-pyrrole 5b) of metallic Lewis acids such as $TiCl_4$, $SnCl_2$, $SnCl_4$ $ZnCl_2$, $AlCl_3$, $BF_3$ in solvents including pyridine can be used.[11]

[9]*Bioorganic & Medicinal Chemistry Letters* 2007, 17, 3814-3818; *Bioorganic & Medicinal Chemistry Letters* 2007, 17, 3819-3825; US20050090541.
[10]US20050090541A1.
[11]WO2008067756A1.

Part 2: A Summary of the Prior Art for Sunitinib Synthesis

The retrosynthesis of sunitinib shown in Scheme 2 shows that it can be synthesised using the standard base catalysed coupling of a 2-pyrrolone (more specifically a 2-indolinone) and a 2-formyl-pyrrole. The amide unit positioned at C4' of the pyrrole can be formed by a standard amide coupling before, after or during the base catalysed coupling of the 2-pyrrolone and 2-formyl-pyrrole units. Indeed, this general approach is disclosed in various permutations in the literature.

Scheme 2-Synthesis of sunitinib (1)

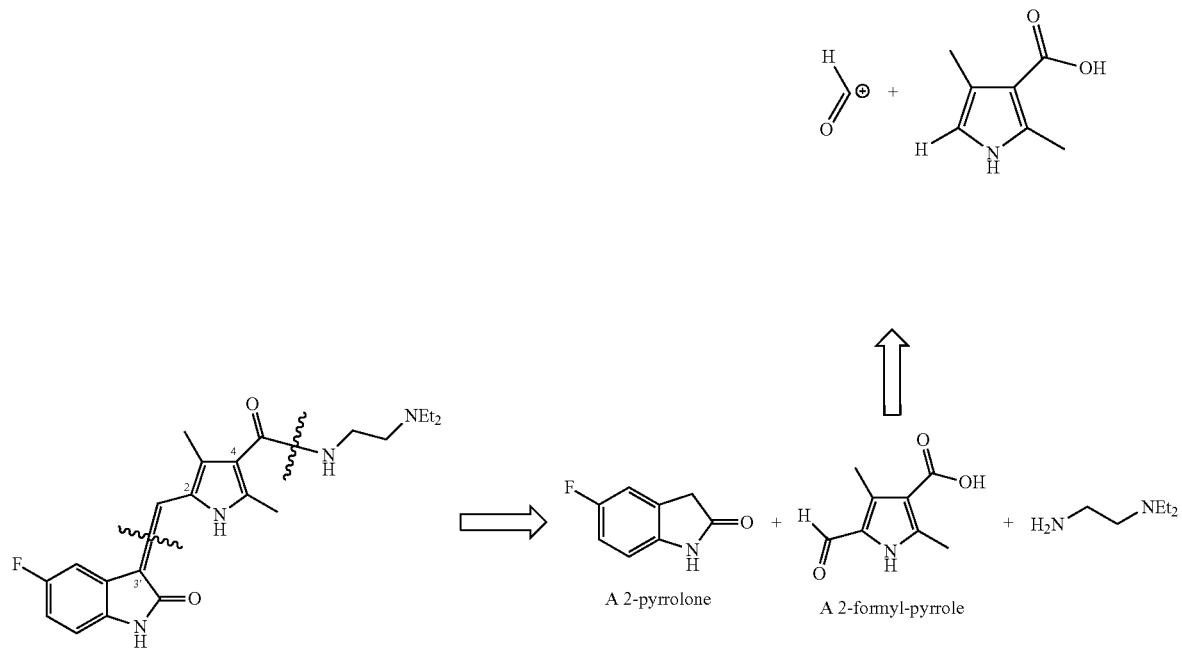

The first synthesis of sunitinib was disclosed by Sugen, Inc. in 2001 (Scheme 3).[12] The synthesis involved the coupling of 2-indolinone 8 with the 2-formyl-pyrrole 13 with the C4' amide functionality already intact.

[12]WO2001060814A2 and *Drugs Future* 2005, 30, 785-792.

Scheme 3-Sugen, Inc.'s original synthesis of sunitinib

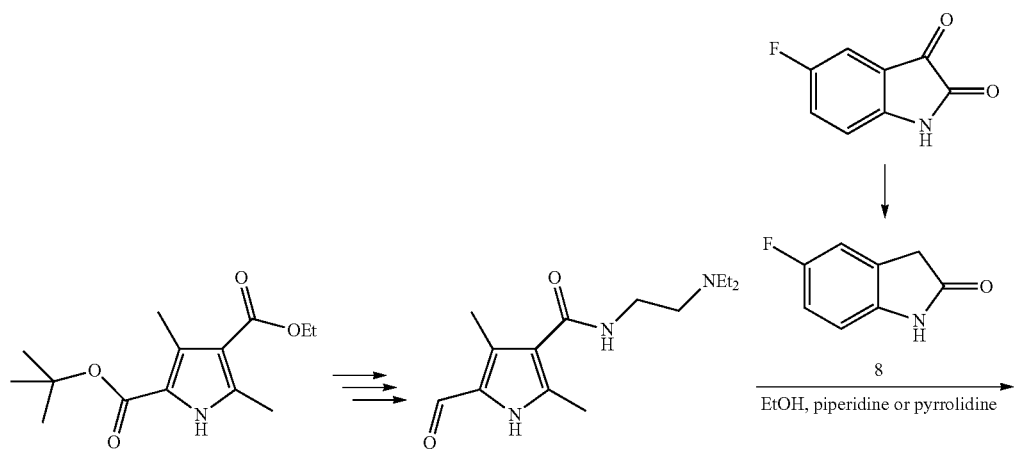

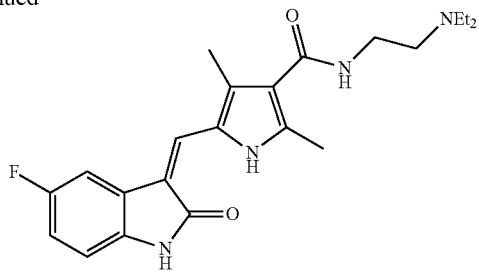

1

Later Pharmacia & Upjohn[13] (Scheme 4) synthesised sunitinib using a one-pot, three-component approach (amine, 2-indolinone and 2-formyl-pyrrole-4-activated carboxylic acid) coupling in the presences of excess Et$_3$N. This route was particularly useful in the drug discovery phase of the project as different analogues could be used, but apparently was not good for scale-up purposes. One problem of this approach was that since the amidation reaction was performed on the activated carboxylic acid which also possessed an aldehyde group, in situ imine formation also occurred providing reaction intermediate 9 and therefore a >2 eq. excess of diamine 7 was required which increased costs and led to work-up problems. Also the use of an activating group (in this case imidazole) and the previously mentioned need for an excess amine 7 were both not considered good on grounds of atom economy.

[13] US20030229229A1.

Scheme 4-Pharmacia & Upjohn's synthesis of sunitinib

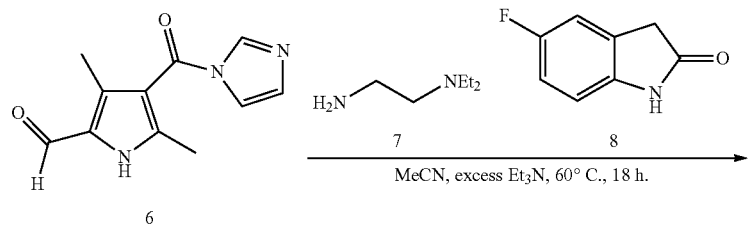

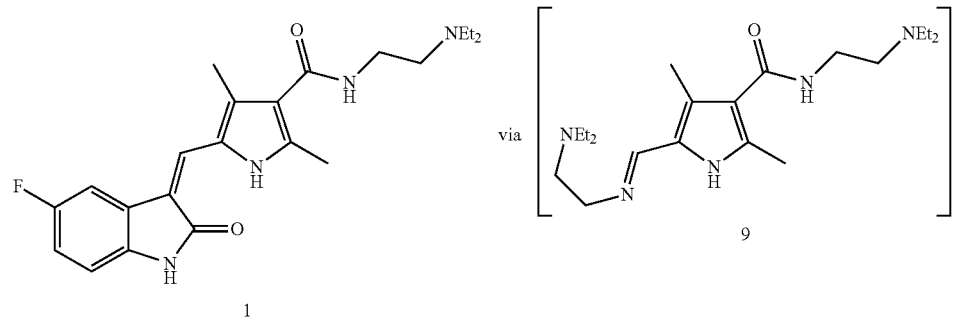

A second synthesis of sunitinib was disclosed by Pharmacia & Upjohn[14] that utilised a similar, in that it was a base catalysed coupling, but more atom economic approach (Scheme 5). The pyrrole starting material synthesis was improved, and instead of providing a 2-formyl-pyrrole it gave a pyrrole, viz., 10, lacking a C2 substituent. The pyrrole 10 was then converted to an iminium salt 12, by reaction with the Vilsmeier salt 11, which could be converted in situ into sunitinib (1). The iminium salt 12 is simply an activated form of Sugen, Inc.'s 2-formyl-pyrrole 13. One draw back to this route is that the synthesis and use of Vilsmeier salts on large scale can be potentially hazardous.[15] Later, this general synthetic approach was modified to make deuterium-enriched analogues of sunitinib.[16]

[14] US20060009510A1; *J. Org. Chem.* 2003, 68, 6447-6450.
[15] *Organic Process Research & Development* 2005, 9, 982-996.
[16] US20090062368A1.

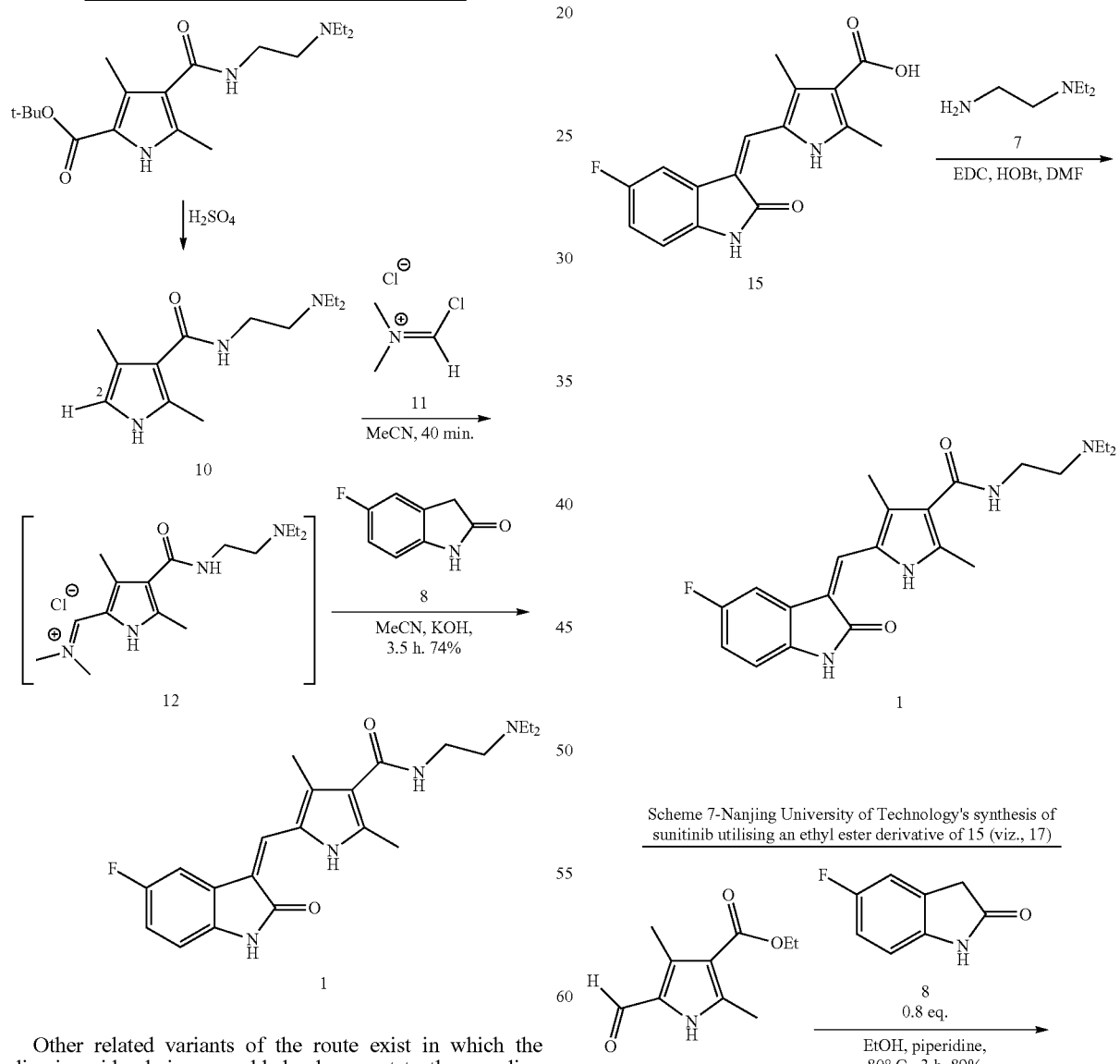

Other related variants of the route exist in which the diamino side chain was added subsequent to the coupling step, and are shown in Scheme 6,[17] 7[18] and 8.[19]

[17] *J. Med. Chem.* 2003, 46, 1116-1119.
[18] CN101333215A.
[19] US20090247767A1; WO2009124037A1.

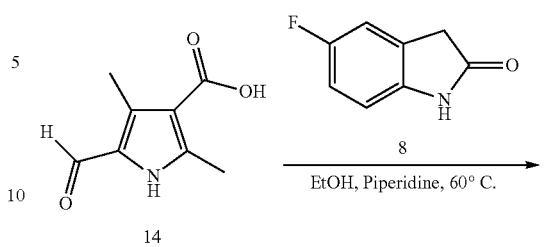

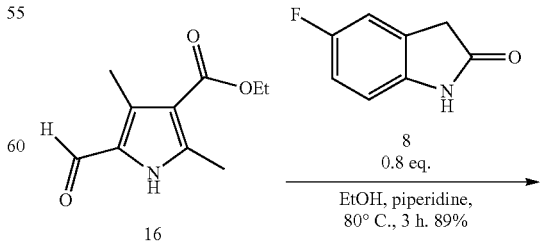

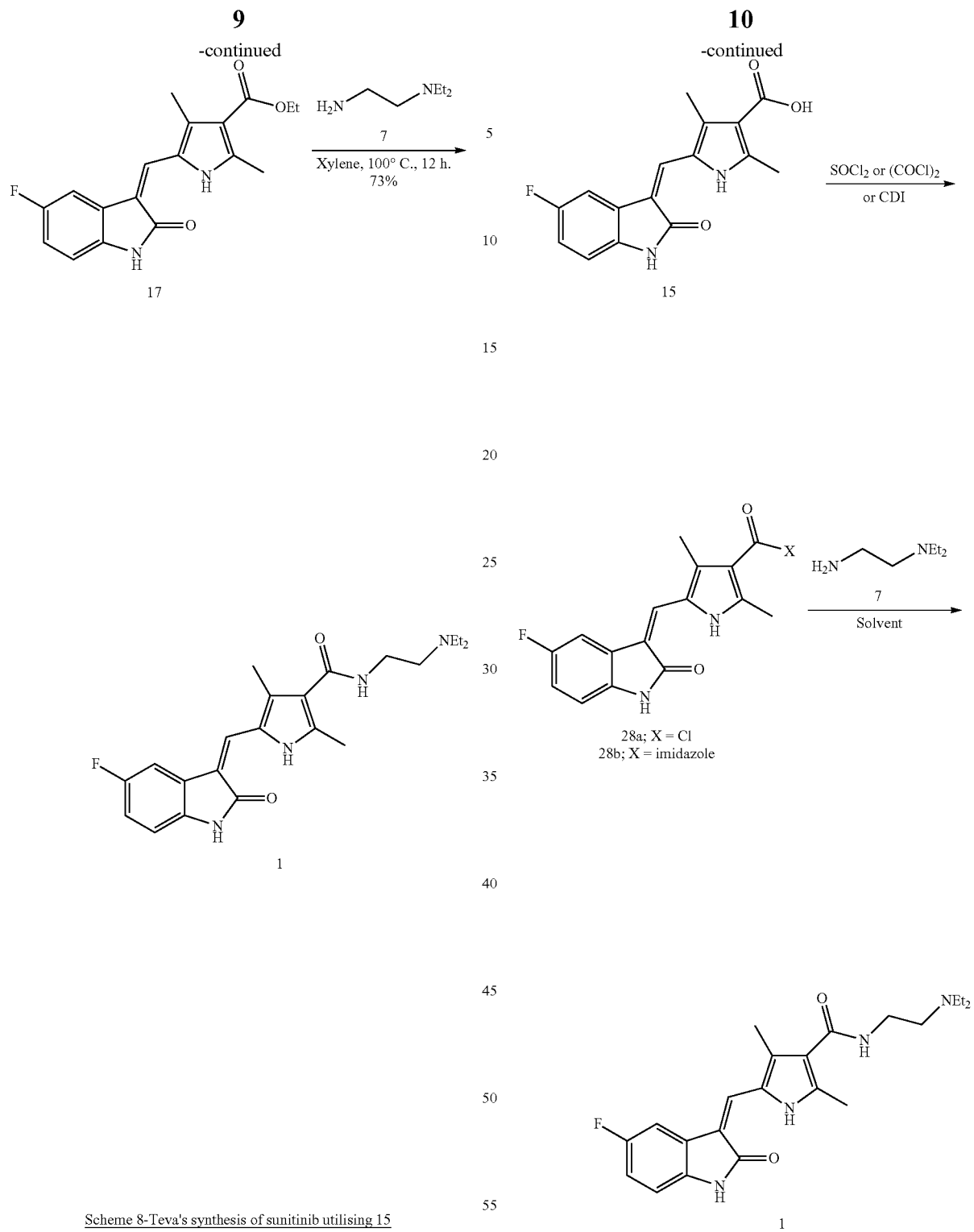

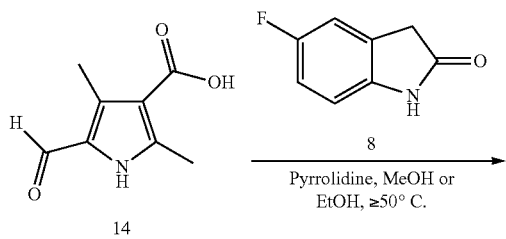

Scheme 8-Teva's synthesis of sunitinib utilising 15

The least similar approach of all for sunitinib synthesis was disclosed by Generics [UK] Limited[20] (Scheme 9). They synthesised sunitinib with 94-96% HPLC purity using either of two routes. One route utilised amide 10 and the other utilising the carboxylic acid 29 followed by amide coupling with diamine 7. The key difference with their approach and all of the other approaches was that the requisite formyl functional group was positioned on the 2-indolinone ring, rather than on the pyrrole ring.

[20] WO2010001167.

Scheme 9 - Generics [UK] Limited's alternative synthesis of sunitinib

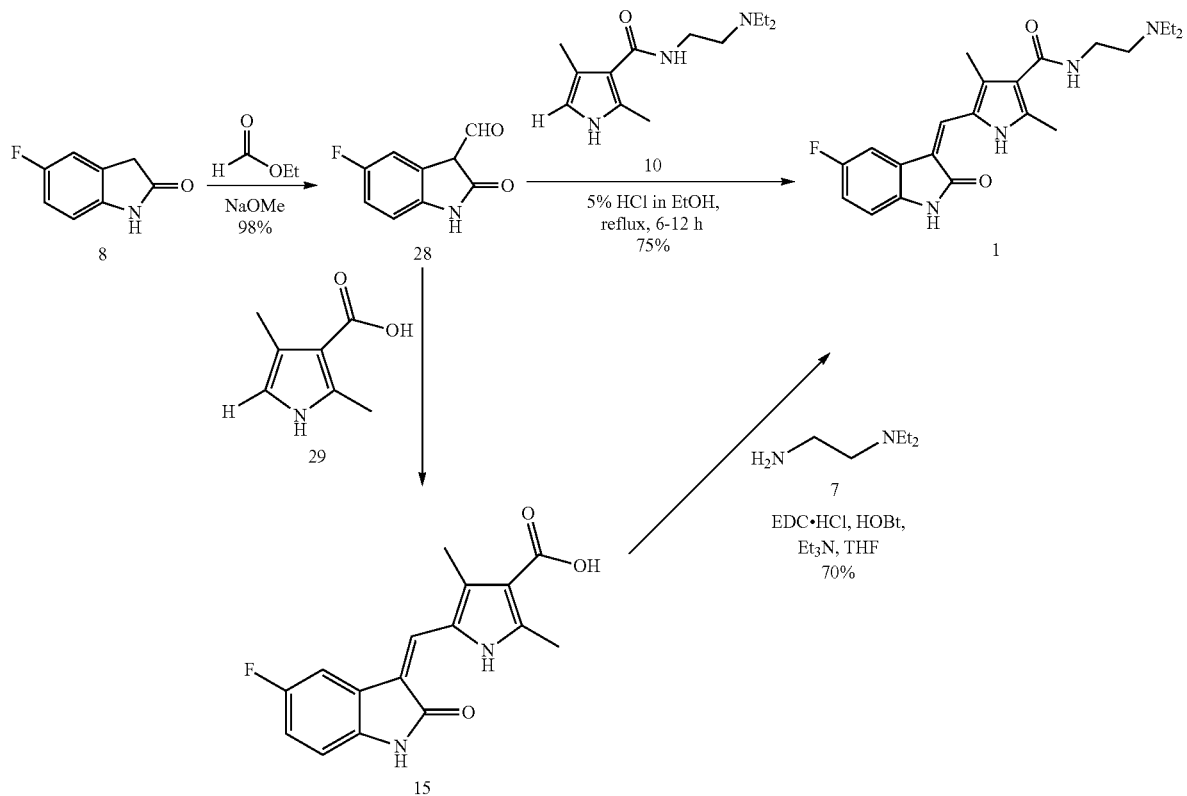

In a modification on Sugen, Inc.'s original route (Scheme 3), Medichem, S.A.[21] by-pass sunitinib free base and directly obtain sunitinib malate (2), which they claim is advantageous. In their approach the malic acid salt of compound 13 (18), "which is a new compound that has not been previously described", is coupled directly with 8 to furnish the API, viz. sunitinib malate (Scheme 10). They state that "the process of the invention is rapid, concise, and avoids the obtaining, isolation, and processing of sunitinib base, and hence overcomes one or more of the drawbacks associated with the lower solubility profile and difficult handling of solid sunitinib base.".

[21]US20090318525A1.

Scheme 10 - Medichem, S.A.'s direct synthesis of sunitinib malate

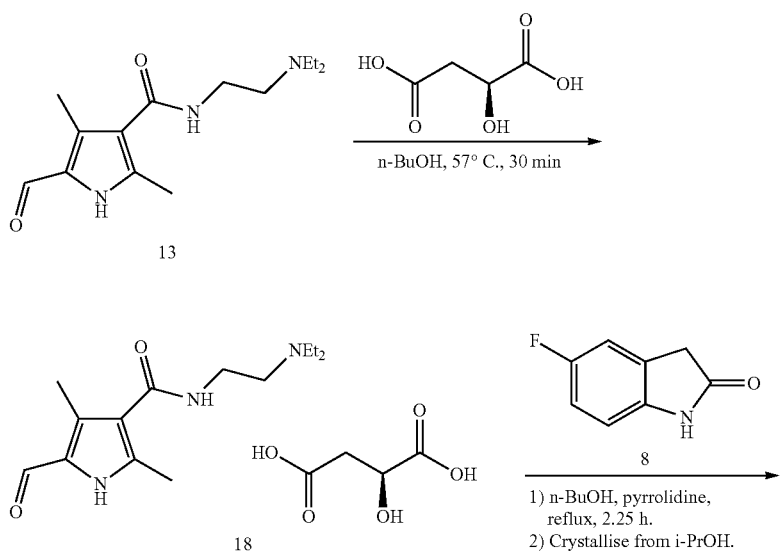

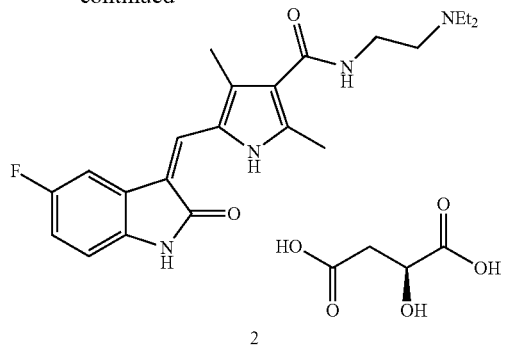

DETAILED DESCRIPTION OF THE PRESENTLY PREFERRED EMBODIMENTS

Part 3: Description of Embodiments

Figure 1:
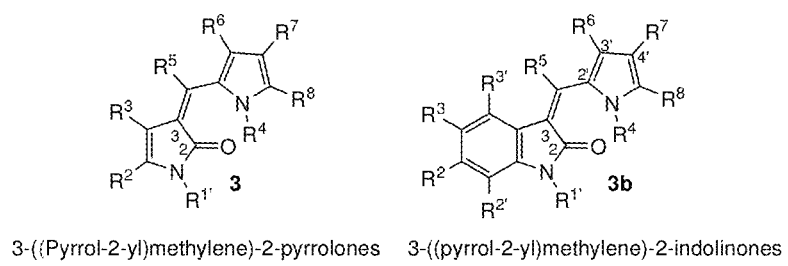
FIG. 1—shows the chemical structures of 3-((pyrrol-2-yl) methylene)-2-pyrrolones.
Figure 2:
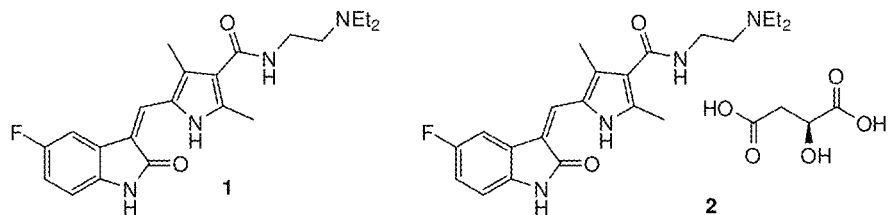
FIG. 2—shows the chemical structures of Sunitinib base 1 and sunitinib malate 2.
Figure 3:
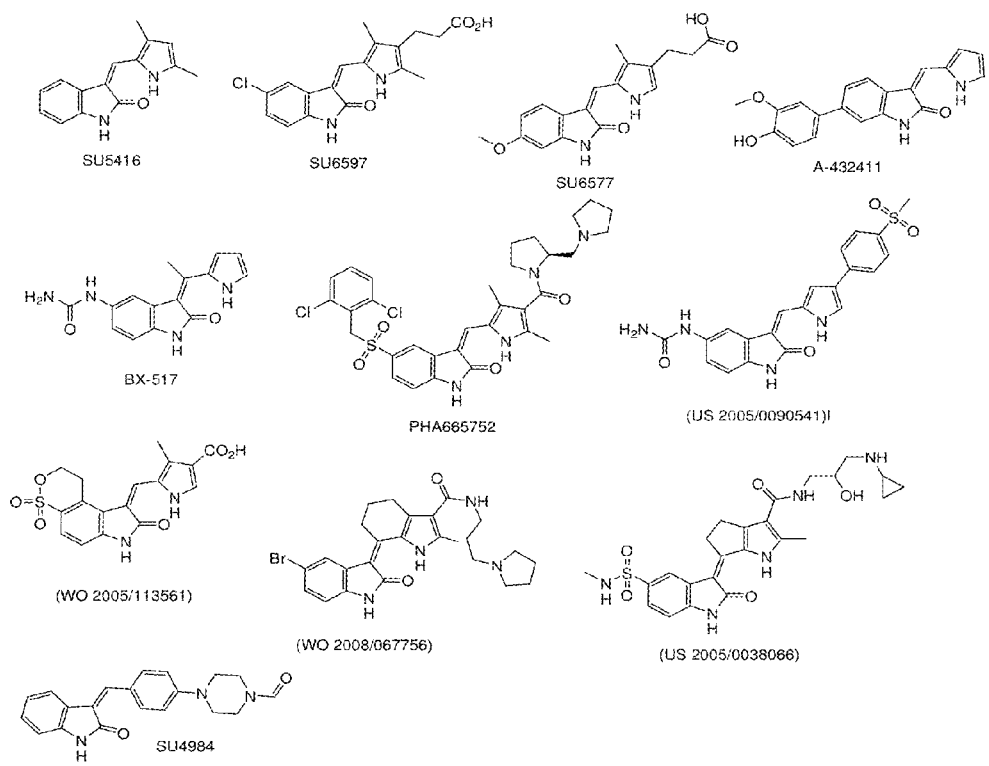
FIG. 3—shows biologically active compounds that possess the 3-((pyrrol-2-yl)methylene)-2-pyrrolone or 3-((aryl)methylene)-2-pyrrolone moiety.
Figure 4:
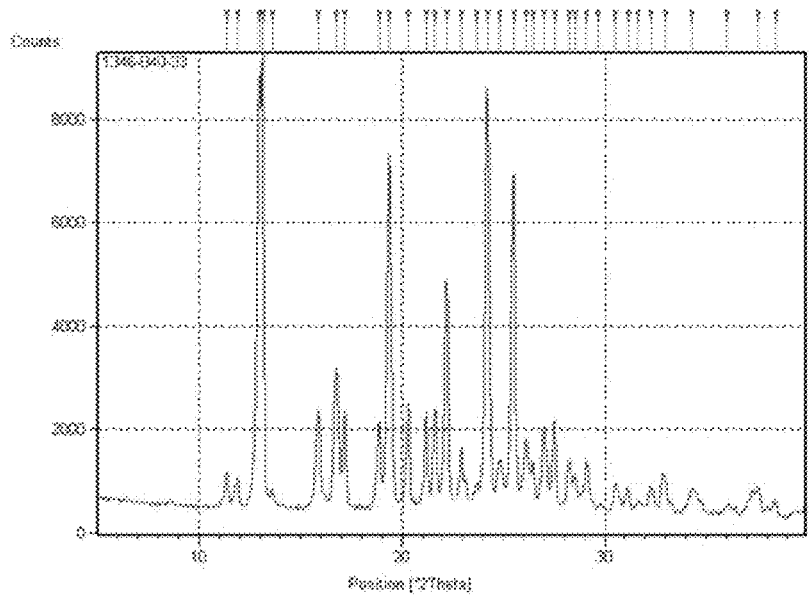
FIG. 4—shows the X-ray powder diffraction XRPD pattern of sunitinib malate crystallised from DMSO and MIBK in this invention.
Figure 5:
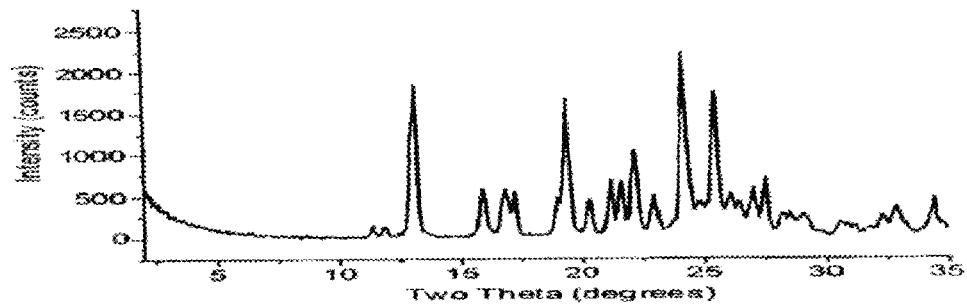
FIG. 5—shows the X-ray powder diffraction XRPD pattern of sunitinib malate polymorph Form I (US2007191458A1)

In the preferred embodiment of this invention silylated 2-pyrrolones 19 (a.k.a., 2-silyloxy-pyrroles), which are activated forms of 2-pyrrolones 4, are coupled with 2-carbonyl-pyrroles 5, such as 2-formyl-pyrroles 5a (i.e., $R^5$=H) and 2-acyl-pyrroles 5b (i.e., $R^5 \neq H$), to afford 3-((pyrrol-2-yl)methylene)-2-pyrrolones 3 (Scheme 11). In a preferred embodiment, and in contrast to the prior arts in related couplings with 2-formyl-pyrroles, an acidic catalyst in the absence of a base catalyst is used to enhance the rate of the reaction. Lewis acids and Brønsted acids can be used in the reaction in a range of solvents under a range of temperatures.

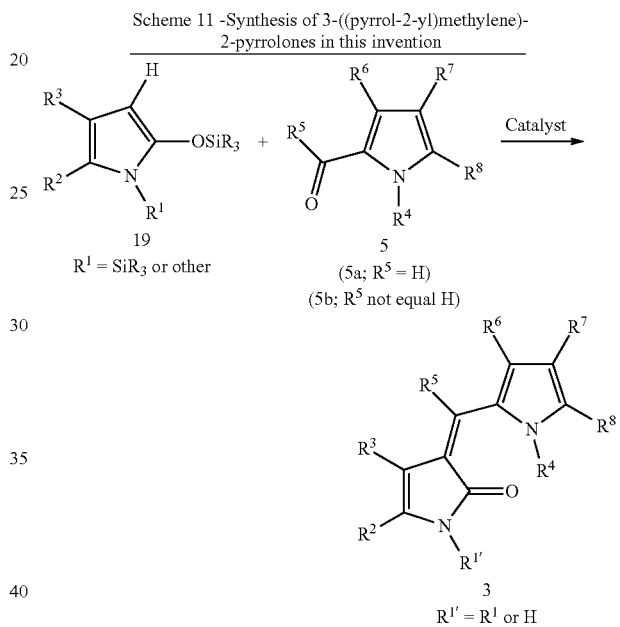

Scheme 11 -Synthesis of 3-((pyrrol-2-yl)methylene)-2-pyrrolones in this invention It is known in nucleoside synthesis that silylated heterocycles are better nucleophiles than their non-silylated derivatives or their O-alkylated derivatives, and that they show improved solubility (Vorbrüggen H. and Roh-Pohlenz C., "Handbook of Nucleoside Synthesis", John Wiley & Sons, Inc., 2001, ISBN 0-471-09383-1.). Also, because silyl groups including TMS group are highly mobile, the thermodynamically most stable silylated heterocycles are produced upon silylation. These phenomena are utilised in a well known nucleoside synthetic protocol referred to as the Vorbrüggen glycosylation. In the coupling reaction step of the Vorbrüggen glycosylation it is accepted that the acid catalyst promotes the removal of the carboxylate leaving group from the C1 position (a.k.a., anomeric position) of the sugar (21) to form an oxonium ion (22) that then reacts with an O-silylated heterocycle 23 to provide the nucleoside product 24 (top scheme, Scheme 12). The oxonium ion 22 can be considered as an intramolecularly alkylated aldehyde. Whilst investigating the Vorbrüggen glycosylation for other purposes, the inventors realised that a similar type of coupling using silylated 2-pyrrolones 19 and 2-formyl-pyrroles 5a (i.e., $R^5$=H) and 2-acyl-pyrroles 5b (i.e., $R^5 \neq H$), in which the carbonyl group could be activated to nucleophilic attack be either i) O-silylation or other Lewis acid coordination, or ii) O-protonation, or iii) by iminium salt formation, should be possible (bottom scheme, Scheme 12). For activation modes i and ii, Lewis acids including trimethylsilyl trifluoromethanesulfonate (TMSOTf) or Brønsted acids could be used. For mode iii several approaches were considered including: a) direct iminium salt formation using a secondary amine, or b) imine formation using a primary amine followed by N-alkylation for form the iminium salt, or c) reaction of a C2-unsubstituted pyrrole with a Vilsmeier salt. Activation of carboxyl ester group by silylation using TMSOTf is commonly used in nucleoside chemistry, as developed by Helmut Vorbrüggen.[22]

[22]Vorbrüggen H. and Roh-Pohlenz C., "Handbook of Nucleoside Synthesis", John Wiley & Sons, Inc., 2001, ISBN 0-471-09383-1, pg 15.

In another embodiment of this invention, silylated 2-pyrrolones 19 can be used in the coupling with iminium salts 5c, derived from 2-formyl-pyrroles 5a or 2-acyl-pyrroles 5b by reaction with amines 36 (preferably acid salts of dialkylamines 36a or primary amines 36b followed by alkylation) or from 2-unsubstituted-pyrroles 37 by reaction with substituted chloroiminium salts 38 (such as the Vilsmeier reagent), to afford 3-((pyrrol-2-yl)methylene)-2-pyrrolones 3 (Scheme 13). Of note, the coupling of 5c should be conductible in the absence of a Lewis or Brønsted acid catalyst because the former carbonyl reactive centre of 5a or 5b is in this mode of the invention already activated as an electrophile.

Scheme 12 - Analogy of nucleoside synthesis (top) and the Mukaiyama aldol addition (middle) to SPK's synthesis of 3-((pyrrol-2-yl)methylene)-2-pyrrolones (bottom)

Vorbrüggen glycosylation:

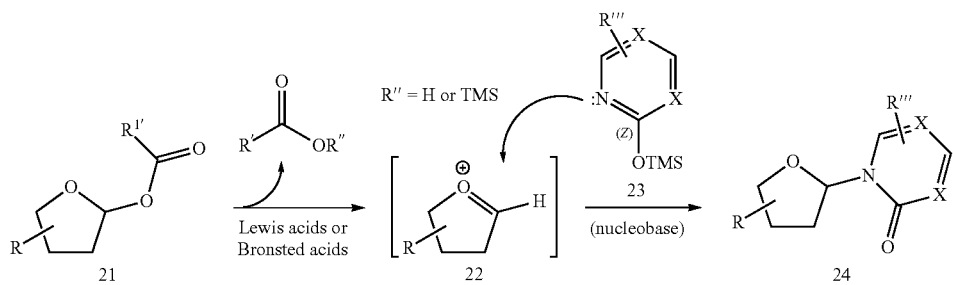

SPK's synthesis of 3-((pyrrol-2-yl)methylene)-2-pyrrolones:

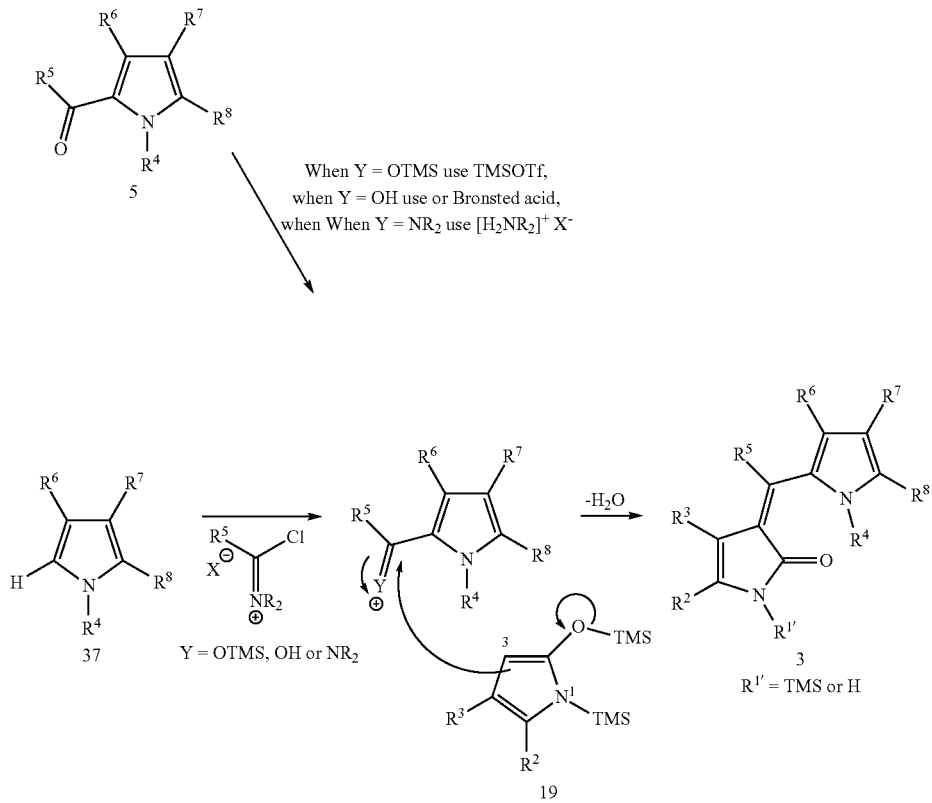

Scheme 13 - Synthesis of 3-((pyrrol-2-yl)methylene)-2-pyrrolones using activated aldehydes

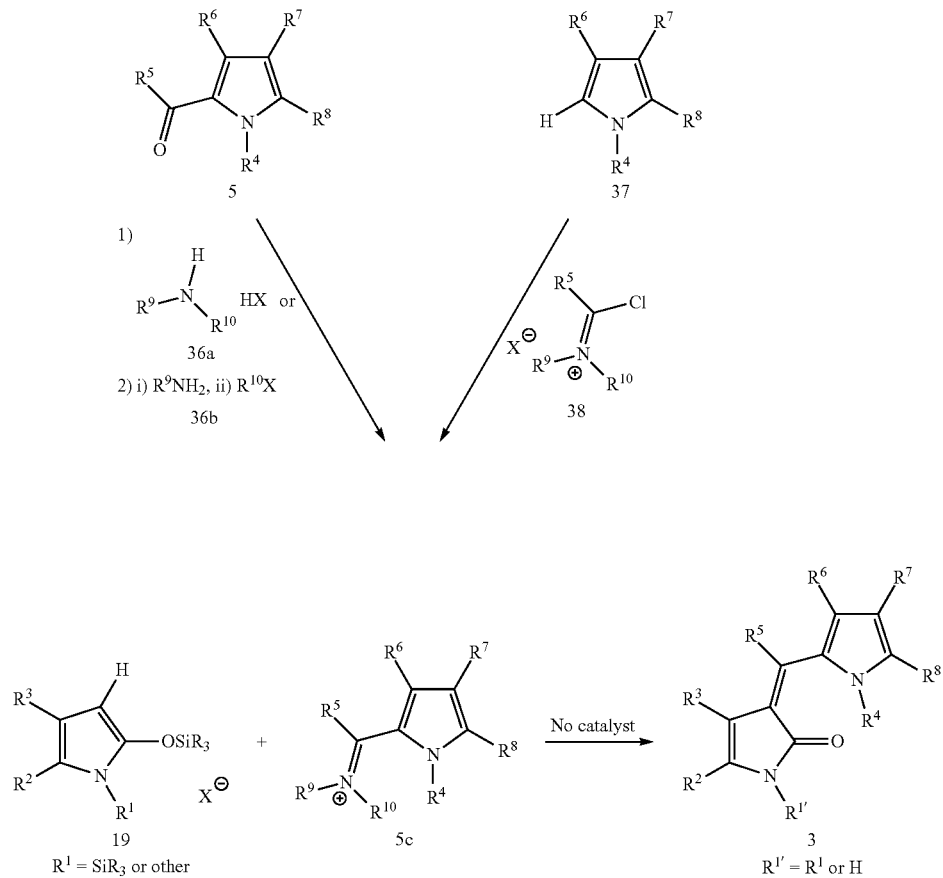

In yet another embodiment of this invention, silylated 2-pyrrolones 19 can firstly be reacted with substituted chloroiminium salts 38 (such as the Vilsmeier reagent) to form iminium salts 39. The iminium salts 39 can then be reacted with 2-unsubstituted-pyrroles 37 to afford 3-((pyrrol-2-yl)methylene)-2-pyrrolones 3 (Scheme 14). As the embodiment shown in Scheme 13, the coupling could be conducted in the absence of a Lewis or Bronsted acid catalyst. This embodiment is a reversal in the order of attachment of the methylene group of the embodiment shown in Scheme 13.

Scheme 14 - Synthesis of 3-((pyrrol-2-yl)methylene)-2-pyrrolones using a reverse approach

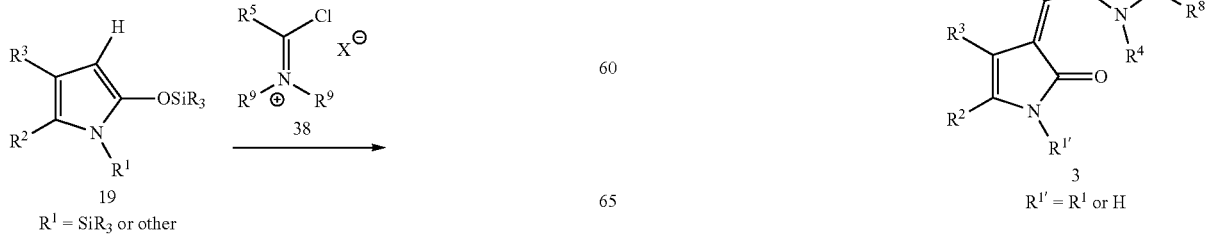

-continued

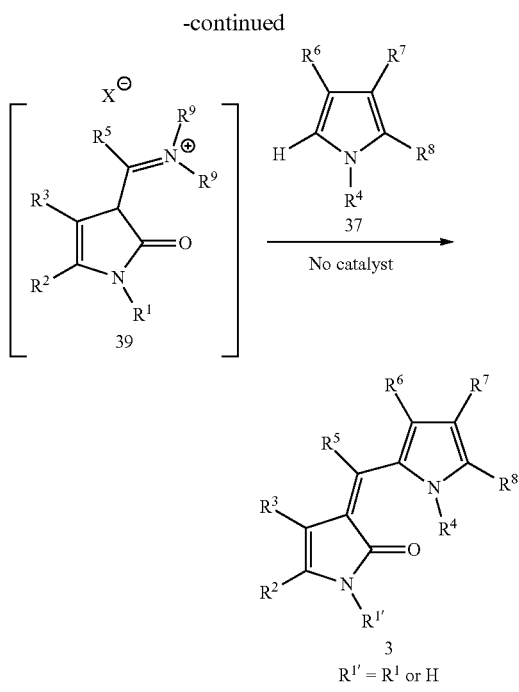

In all of these embodiments, pyrrole/pyrrolone units are bridged by a methylene unit in which the aldehyde, ketone, iminium salt or chloroiminium salt is a masked methylene group.

Part 4: A Summary of this Invention with Focus on the Synthesis of Sunitinib (1)

Specifically we have focused the application of this invention towards the synthesis of sunitinib (1). Sunitinib, and in particular its L-malic acid[23] salt 2, has received a significant amount of attention in patent literature over the last decade, particular in the last several years, both in terms of its synthesis but also its crystalline forms and ways to prepare these. This invention is primarily concerned with its synthesis. As with most of the syntheses of sunitinib there are two main approaches which simply reflect whether a key amide bond is formed before or after the two pyrrole units are bridged together through the methylene bridge. We have called these Approaches 2 and 4 (Scheme 16). Another approach, Approach 5, that is similar to Approach 2 is also discussed below.

[23] From hereon in for convenience we refer to L-malic acid, which is the naturally occurring enantiomer, as malic acid.

In Approach 4 the diamino side chain is added subsequent to the coupling step, and thus silylated 2-pyrrolone 20 is coupled with 2-formyl-pyrrole compound 14 which possesses an unprotected carboxylic acid group. Following the coupling step, the 3-((pyrrol-2-yl)methylene)-2-indolinone 15 product is then coupled with the diamine 7 to provide sunitinib. In Approach 2 20 is coupled with 2-formyl-pyrrole compound 13, in which the amide functional group is already installed. The crude sunitinib made using this latter approach (i.e., Approach 2) of our invention is of high purity and does not need purification when using our best mode conditions. The minimum HPLC purity of optimized mode of Approach 2 crude sunitinib is ≥98.5%, but is typically ≥99.0% with no individual impurities detected at >0.30%. The high purity aspect of our invention is crucial since sunitinib is poorly soluble and its purification is not efficient in terms of impurity removal efficiently with respect to recovery yield. Moreover, converting sunitinib of ≤98.5% HPLC purity to its malic acid salt provided sunitinib malate (2) that was difficult to further enrich to API grade material efficiently, therefore it was paramount that our process furnished high purity crude sunitinib base (1). The crude unpurified sunitinib from Approach 2 can be used to synthesise its malate salt 2, the ingredient used in SUTENT®, which after a single recrystallisation meets the purity specification required for human consumption, and is ≥99.5% purity by HPLC but is typically ≥99.7% with no individual impurities detected at >0.15%.

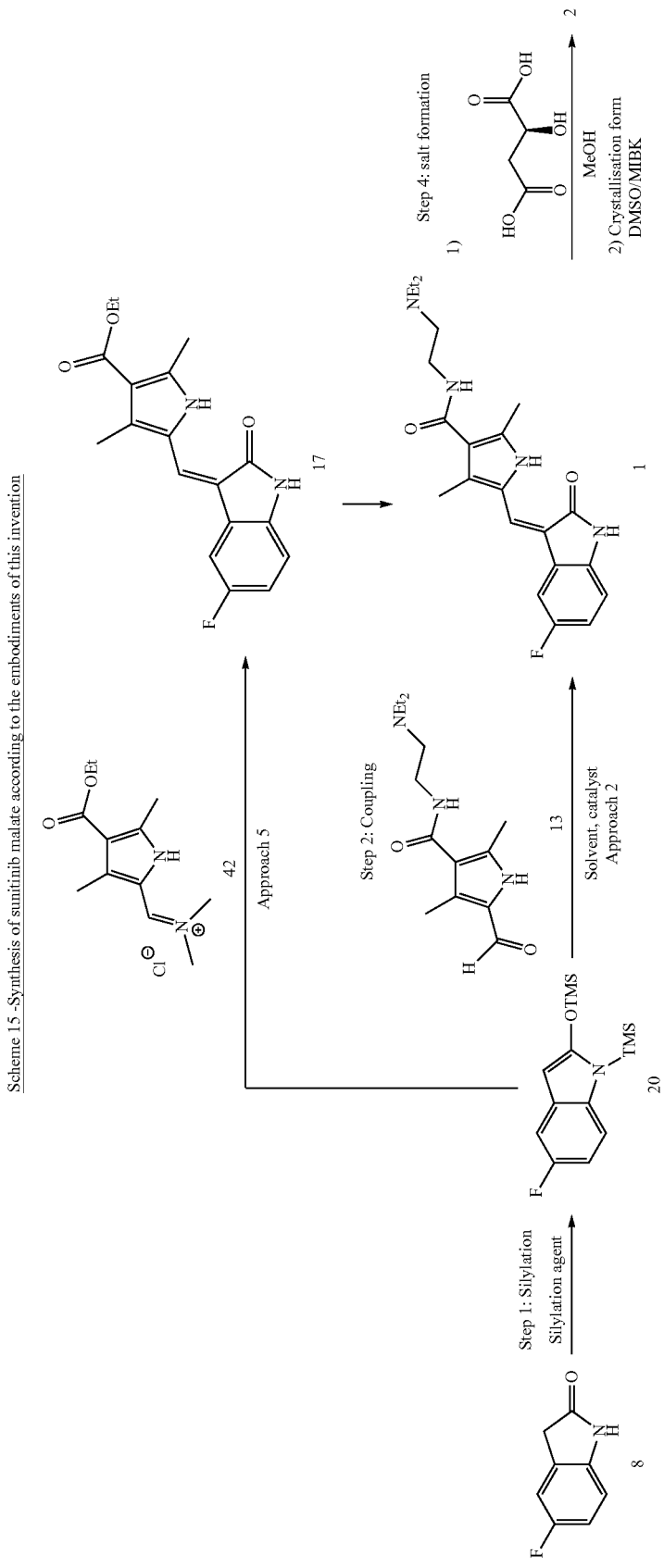

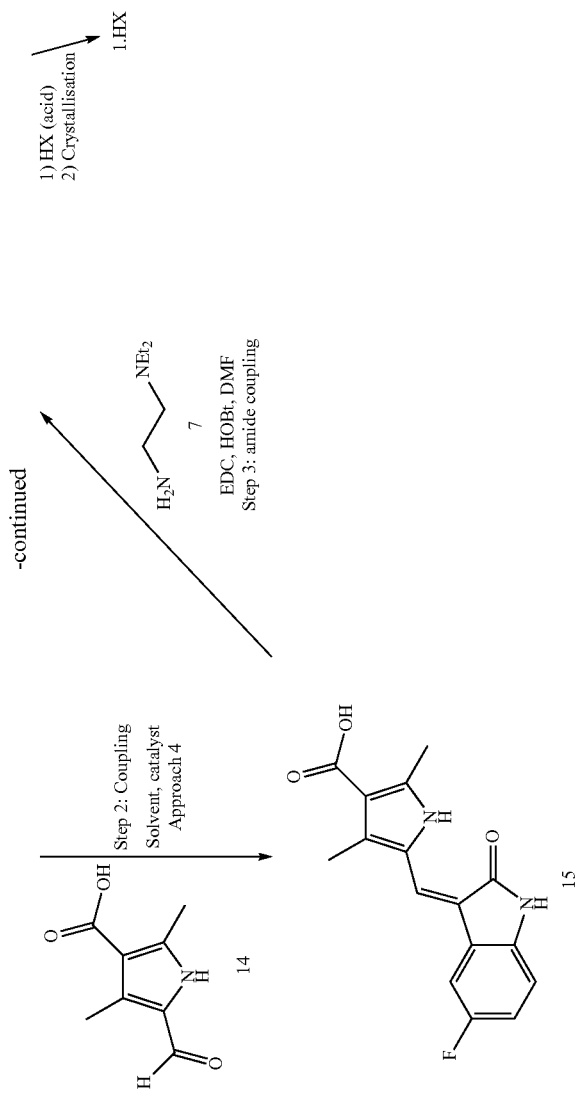

Approach 2 and 4—Step 1—silylation: In the first step, 2-indolinone 8 is silylated using a silylating agent to furnish a bis-silylated compound that is believed to be N-trimethylsilyl-2-(trimethylsilyloxy)-indole 20. This compound was confirmed to possess two trimethylsilyl (TMS) groups by GCMS analysis, and we assume that the structure is most likely as drawn and for convenience will be represent as structure 20. Both N,O-bis(trimethylsilyl)trifluoroacetamide (BSTFA) and hexamethyldisilazane (HMDS) can be used independently to silylate 8 to provide 20. Other silylating agents such as trimethylsilyl chloride (TMSCl) and N,O-bis(trimethylsilyl)acetamide (BSA) as well as combinations of all mentioned might also be applicable. The silylating agent can be used in solution with a co-solvent, including MeCN or THF, or neat with the silylating agent behaving as a solvent itself. When BSTFA is used only 3 molar equivalents are typically required, MeCN solvent is used (but others including THF can be used) and the reaction is typically conducted at reflux. When HMDS is used 9 molar equivalents are typically required along with a catalytic amount of $(NH_4)_2SO_4$, no co-solvent is used and the reaction is typically conducted at reflux.

Approach 2 and 4—Step 2—solvents: The second step, viz., the coupling step, can be conducted as a one-pot reaction in conjunction with the silylation step, or it can be conducted as a separate step. When the two steps are conducted in one-pot the solvent from the first step, if one was used, acts as a solvent in the second step or an additional solvent can be added. When the two-pot process is used and crude 20 was used in the coupling with either 13 or 14 using TMSOTf as a catalyst, acetone, DCE DCM, $CHCl_3$, PhMe, DMF, EtOAc, MeCN, n-heptane, dioxane, acetone, MIBK, and THF can be all used. MeCN and DMF provided the fastest reactions and gave among the best sunitinib purities in the coupling of 13, but MeCN was preferred based on considering reaction yield, rate and product purity. In the coupling of 14 and 20 to give 15, the reaction times were generally longer but MIBK was preferred based on considering reaction yield, rate and product purity. MeCN was also acceptable in terms of reaction rate, but DCE and DCM were preferred for both yield and purity but reaction times were much longer. When the two-step, one-pot version of Approach 2 is used no solvent needs to be added for Step 2 (coupling) as the excess HMDS from Step 1 acts as the solvent. If the HMDS is not removed following Step 1, as in the two-step, one-pot version, a second solvent can be added but less may be required as the excess HMDS from Step 1 acts as a co-solvent. Prior to the coupling step, it is sometimes preferred that the 13 or 14 is pre-dissolved in a polar solvent such as MeCN, DMF, THF or DMSO, and is then added to a mixture of 20 and the reaction catalyst at the desired reaction temperature, and this can help control impurity formation. In this mode, it is preferred that a DMF solution 13 is added dropwise to the other reactants (i.e. 20 and catalyst in reaction solvent with heating) over an extended period of time such as several hours because this helps minimise impurity formation. When BSTFA is used as the silylation reagent in MeCN in Approach 2, Step 1 the crude solution can be used directly in Step 2 with only the addition of some more MeCN, TMSOTf and 13.

Approach 2—Step 2—catalysts: The catalysts used in the second step can be either Lewis acids or Brønsted acids, however, Lewis acids are most preferred. Besides TMSOTf, however, other Lewis acids such as tert-butyldimethylsilyl trifluoromethanesulfonate (TBSOTf) and those known to work in the Mukaiyama aldol reactions such as $BF_3.Et_2O$, $SnCl_4$, $LiClO_4$, $M(OTf)_n$ (lanthanide and other metal triflates such as $Sc(OTf)_3$ and $Hf(OTf)_4$), and $ZnX_2$ (zinc halides such as $ZnCl_2$ and $ZnI_2$) might be applicable as well as $AlCl_3$, trimethylsilyl methanesulfonate (TMSOMs), and $TiCl_4$.

When the catalyst is TMSOTf, between 0.10 molar equivalents and 1.00 molar equivalents or more can be used, but about 0.2 eq. is preferred. When smaller amounts are used the reaction times become longer, which can be shortened by use of higher temperatures. When the coupling is catalysed by 0.2 eq. of TMSOTf, the coupling reaction at reflux in MeCN is 20 times more rapid than that at r.t., but the yield and purities are similar under the two reaction conditions.

Brønsted acids that can be used in the reaction include carboxylic acids (including malic acid, and thus sunitinib malate (2) is directly isolable if the appropriate work-up is utilised) and halocarboxylic acids (including trifluoroacetic acid (TFA)), mineral acids (including $H_2SO_4$), and sulfonic acids (including toluenesulfonic acid (TsOH), trifluoromethanesulfonic acid (TfOH), methanesulfonic acid (MsOH) and camphorsulfonic acid (CSA)).

Approach 4—Step 2—After using 0.2 eq. TMSOTf as catalyst in the coupling of 20 with 14 the 3-((pyrrol-2-yl)methylene)-2-indolinone 15 product was then coupled with the diamine 7 to provide sunitinib based on method reported in the literature.[24]

[24] *J. Med. Chem.* 2003, 46, 1116-1119.

Approach 2—Step 2—isolation of sunitinib: After the coupling reaction is complete, the reaction mixture is adjusted to 25° C. The resultant slurry can be treated in a variety of different ways including stirring with aq. $NaHCO_3$ (which is our standard and preferred work-up; followed by cooling in an ice bath), or MeOH, or aq. MeOH, i-PrOH, n-butanol, NaOMe in MeOH, water (followed by cooling in an ice bath), $MeNH_2$ in water, $MeNH_2$ in EtOH, or $3HF.Et_3N$, for 0.5 to 3.5 hours then filtration, washing with water and then EtOH to provide after in vacuo oven drying crude sunitinib. The yields and HPLC purities of sunitinib using these methods are consistent and acceptable and the sunitinib does not require crystallisation or any other purification. In one aspect of this embodiment, the quench additive is a solvent that functions to extract impurities from the solid sunitinib into the solution phase before filtration. In this mode, the quench can also be considered a reslurry purification and should be conducted for a period of time that is sufficient to provide a purity enhancement. Alternatively, the reaction product mixture can be acidified to about pH 4-5 causing all solids to dissolve, and then adjusted to pH 8-9 causing the sunitinib to precipitate. It can then be isolated by filtration washed with water and then EtOH, and dried.

Figure 8:
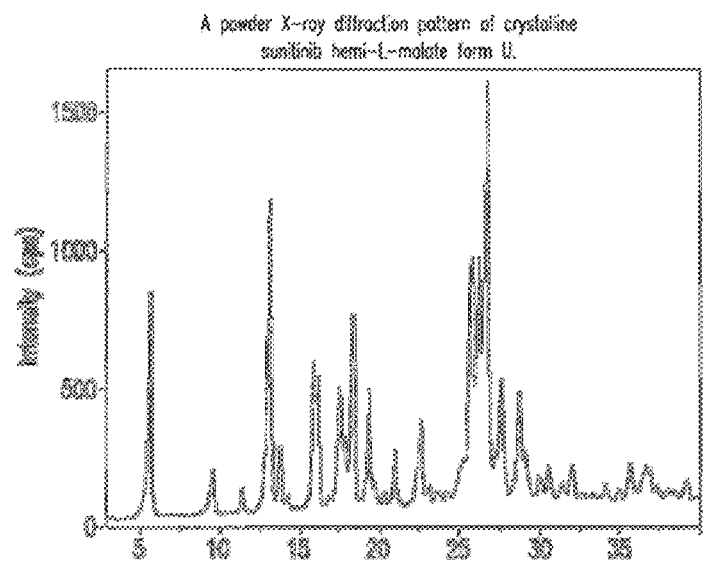
FIG. 8—shows the X-ray powder diffraction XRPD pattern of Form U disclosed in WO2009067686A2.
Figure 9:
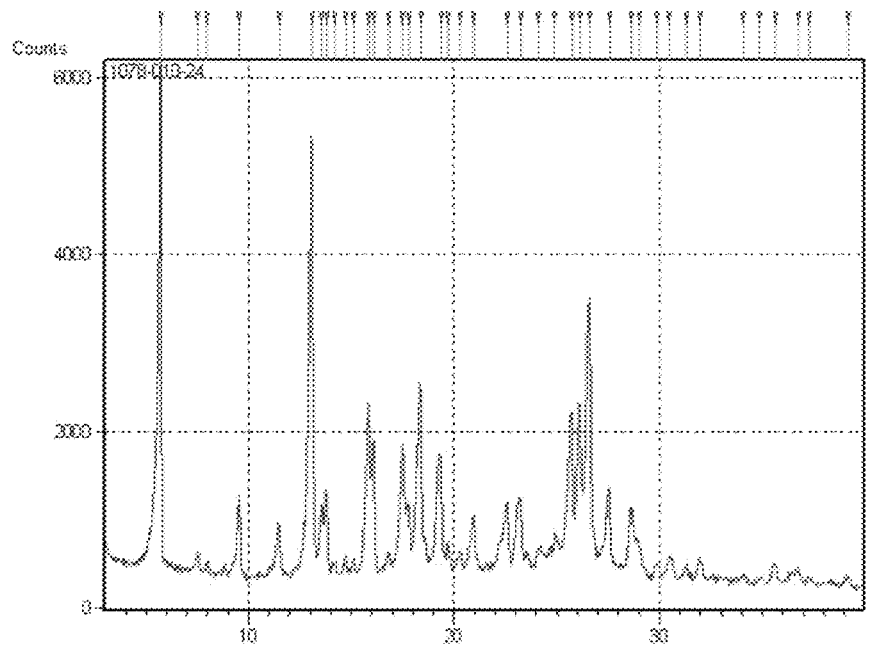
FIG. 9—shows the X-ray powder diffraction pattern of the product made in Example 19.

Directly isolating salts of sunitinib without isolation of sunitinib free base. In addition to isolating sunitinib from Step 2 as its free base form 1, in another aspect of this embodiment sunitinib can also be directly isolated from the completed reaction product mixture as other salts 1.HX (Scheme 16) including its malate (2), camphor sulphonate, tartrate, trifluoroacetate, benzoate, acetate, mesylate, hydrochloride and hydrobromide salts by addition of the appropriate acids (i.e., malic acid, CSA, tartaric acid, trifluoroacetic acid, BzOH, AcOH, MsOH, HCl or HBr, respectively) to the untreated product mixture in typically >97% HPLC purity. The salt forms can optionally be recrystallised if required or purified by reslurry in solvents including alcohols such as n-BuOH or MeOH. The salts can be converted to the free base 1 by treatment with aq. NaOH (or other aqueous bases such as carbonates and bicarbonates) giving free base form 1 typically in >99% HPLC purity Approach 2/4—Step 4—malate salt formation: Sunitinib free base (1) of high purity provided in processes such as Approach 2 can be directly used without prior purification to form sunitinib malate salt (2) by treatment of sunitinib free base with L-malic acid in solvents including MeOH. The salt 2 can then be purified to provide API grade product by crystallisation using a range of solvent combinations. We discovered, however, that a mixture of DMSO and MIBK was preferred to provide high quality 2 with ≥99.5% purity by HPLC and typically ≥99.7% with no individual impurities detected at >0.15%. XRPD analysis shows (FIG. 8) that the product is crystalline and is essentially identical to crystal Form I (FIG. 9).

The use of DMSO and MIBK for the crystallisation of prior art polymorphic Form I of sunitinib malate (2) is disclosed in WO2009104021A2 (Generics [UK] Limited), however, contrary to that in the procedure taught in WO2009104021A2 we discovered that it was important to heat the DMSO to about 45° C. but not more than about 45° C. prior to, but not subsequent to, the addition of the sunitinib malate. In our preferred protocol which was not taught in WO2009104021A2, once the solvent was at this temperature, sunitinib malate could be added allowing quick dissolution, before promptly adding the anti-solvent (MIBK) and then cooling to get the crystals of Form I. Importantly we found that if DMSO temperatures higher than about 45° C. were used, then an increase in the amount of a difficult to remove impurity occurred. Furthermore, the amount of time that sunitinib malate is allowed to reside in hot DMSO should be strictly controlled, otherwise the resultant isolated crystalline product 2 does not meet the purity criteria set for the API due to an increase in the amount of an impurity. This could be essential on manufacturing scales since the time to heat up a solvent could take a long time and lead to degradation of the sunitinib malate, thereby leading to product of inferior and unacceptable quality. Claim 63 in WO2009104021A2 specifies a temperature of between 55-115° C., and EXAMPLE 10 states "A slurry was observed. The reaction mixture was heated to about 55° C. and then maintained at this temperature for about 5-10 minutes. A clear solution was observed". Thus, in the context of the utilisation of a crystallisation from DMSO and MIBK solvent mixture in our invention, WO2009104021A2 has not taught how to avoid the undesirable phenomenon of the impurity formation that we observed. This could be more significant on a manufacturing scale where the time period for unit operations can be significantly increased.

Figure 6:
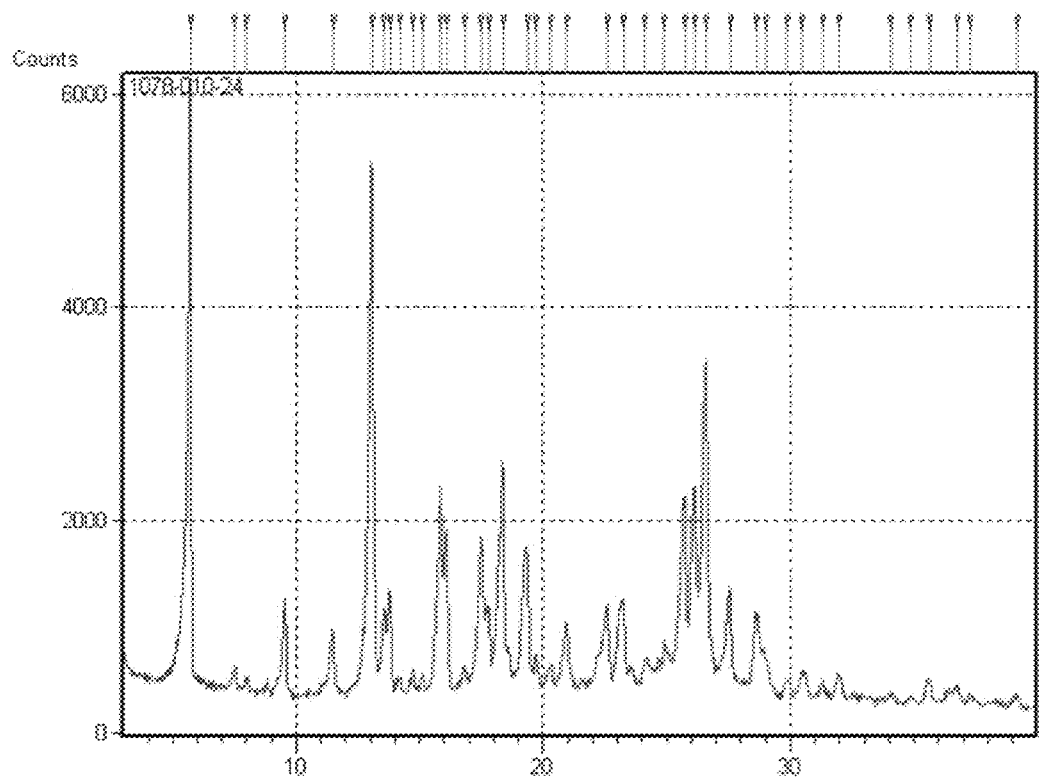
FIG. 6—shows the X-ray powder diffraction XRPD pattern of a crystalline form of sunitinib malate isolated by an embodiment described herein which is consistent with Form U.
Figure 7:
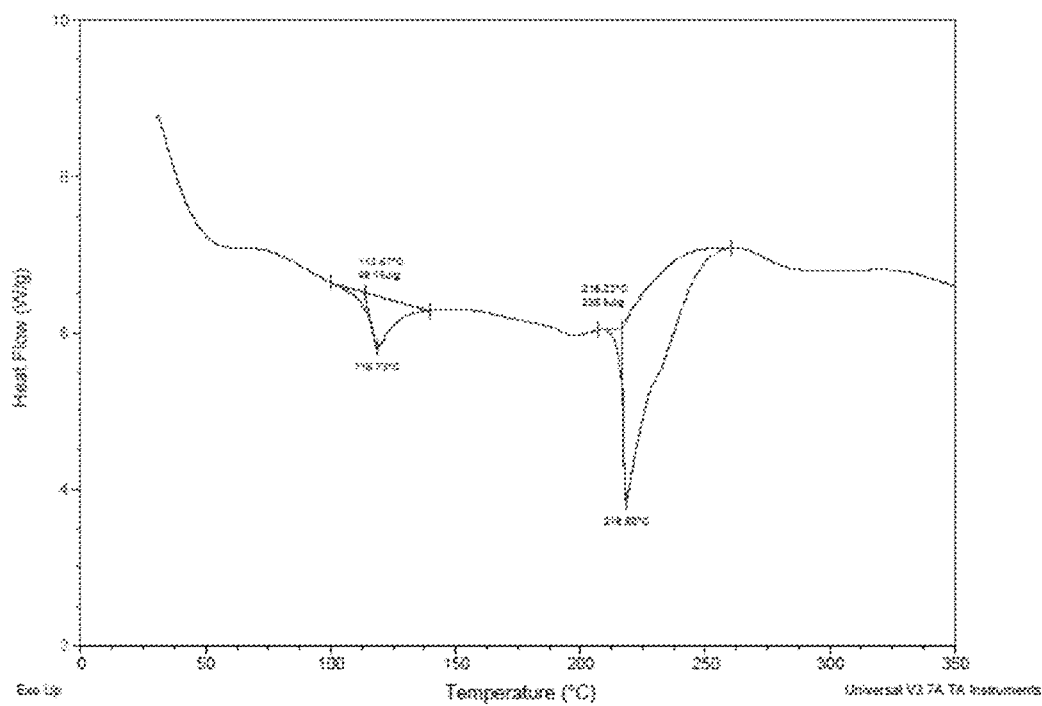
FIG. 7—shows the DSC trace of another crystalline form of sunitinib malate isolated by an embodiment described herein.

To the inventors' surprise, under crystallisation conditions not taught in WO2009067686A2, a crystalline form of sunitinib malate, proposed in WO2009067686A2 to be a sunitinib hemi-malate salt, can be obtained. Specifically, when sunitinib malate prepared in an embodiment of this invention was crystallised from DMSO and MIBK the crystalline form (see FIG. 6) substantially consistent with the form described as Form U (a sunitinib hemi-malate salt; FIG. 8) in WO2009067686A2 was obtained. That the form was not a 1:1 malate salt was confirmed by the detection of a deficit of malic acid in the salt form as indicated by $^1$H NMR spectroscopic analysis and titration. This was a very unexpected discovery because the sunitinib malate salt was used as the starting material in the crystallisation experiment. The DSC trace is shown in FIG. 7. The endothermic peak at about 218° C. is consistent with Form U disclosed in WO2009067686A2 Importantly, the conditions discovered by the inventors, which is an embodiment of this current invention, are much easier to conduct for the preparation of Form U in than those disclosed in WO2009067686A2 and therefore are advantageous.

Approach 5—utilisation of iminium salts: Sunitinib free base (1) can be synthesised by another embodiment of this invention called Approach 5 (Scheme 16). This approach involves the coupling of N-trimethylsilyl-2-(trimethylsilyloxy)-indole 20 with the iminium salt 42. Because the iminium salt 42 is an activated derivative of a 2-formyl-pyrrole, no catalyst is required in the coupling step with 20 (Scheme16). As per that disclosed in CN101333215A, compound 17 can be converted into sunitinib by reaction with diamine 7.

Scheme 16 - Synthesis of sunitinib analogue 17 according to an embodiment of this invention

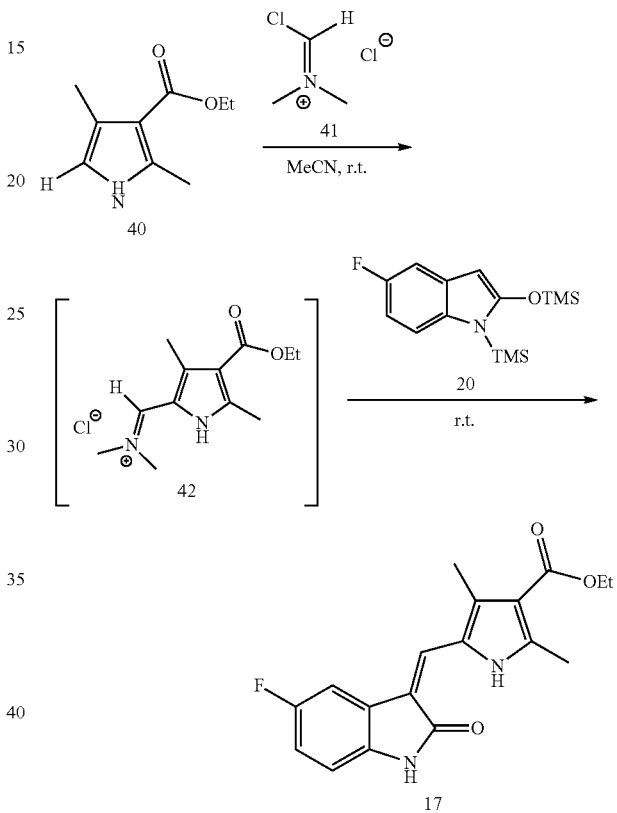

2-Acyl-pyrroles can also be coupled with 2-silyloxy-pyrroles to provide sunitinib analogues. This was demonstrated in the synthesis sunitinib analogue 44 which was prepared by the TMSOTf catalysed coupling of 2-silyloxy-pyrrole 20 with 2-acetyl-pyrrole (43) (Scheme17).

Scheme 17 - Synthesis of a sunitinib analogue 44 from a 2-acyl-pyrrole according to an embodiment of this invention

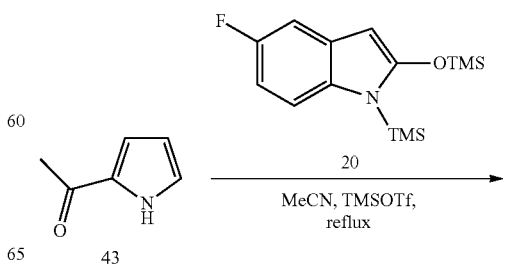

29
-continued
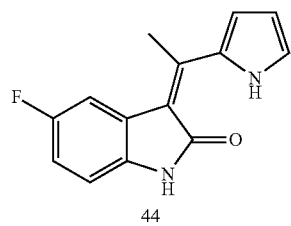
44
Part 5: A Summary of the Embodiments of this Invention
A number of embodiments of this invention have been described above.
These are summarised below.
1) The preferred embodiment (see also Scheme 11).
30
2) Another embodiment closely related to the preferred embodiment (see also Schemes 13, 15, 16 and 17).
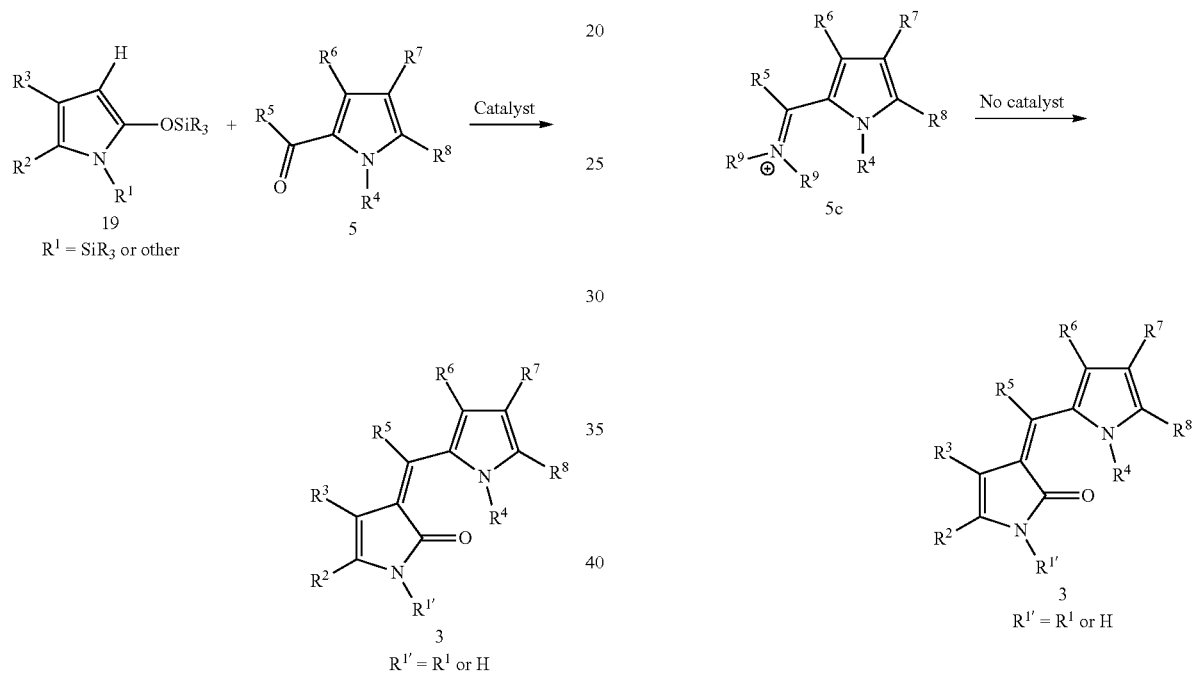
3) An embodiment related to the preferred embodiment (see also Scheme 15).
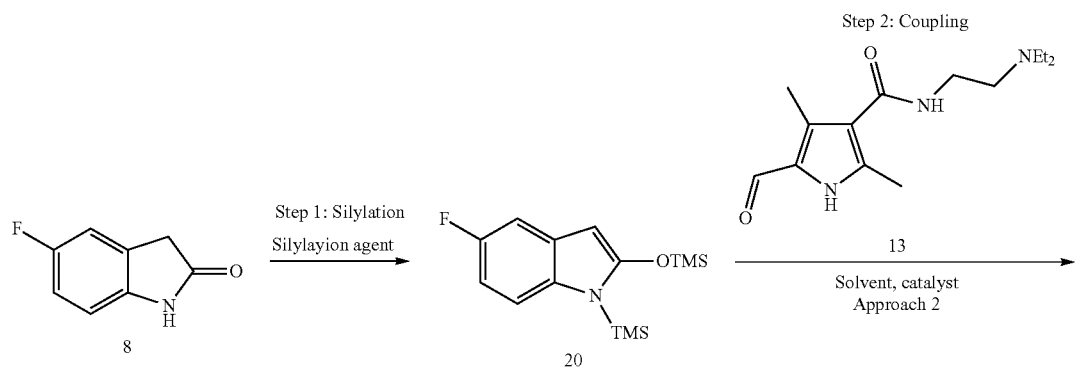

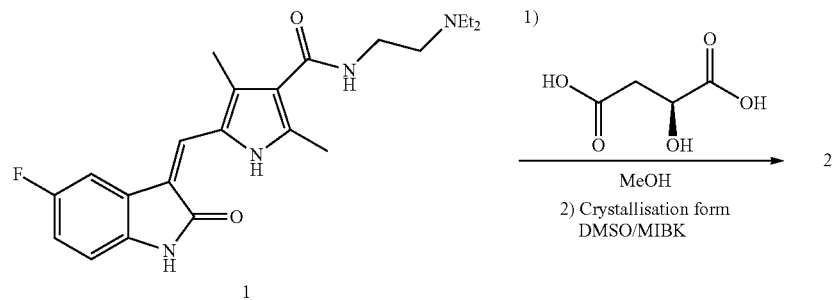
4) Another aspect of the embodiment in part 4 above (see also Scheme 15).
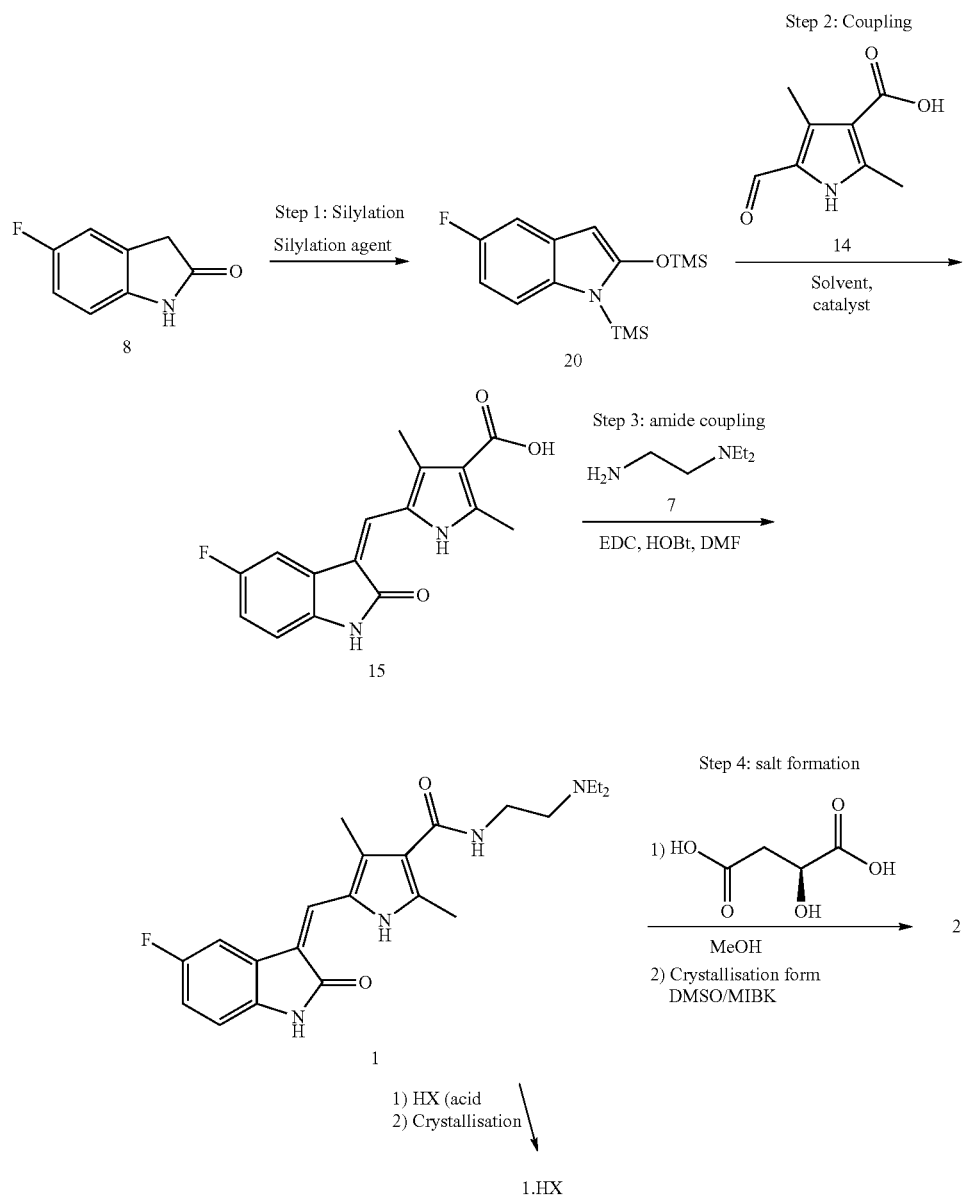

5) Another embodiment (see also Scheme 14).

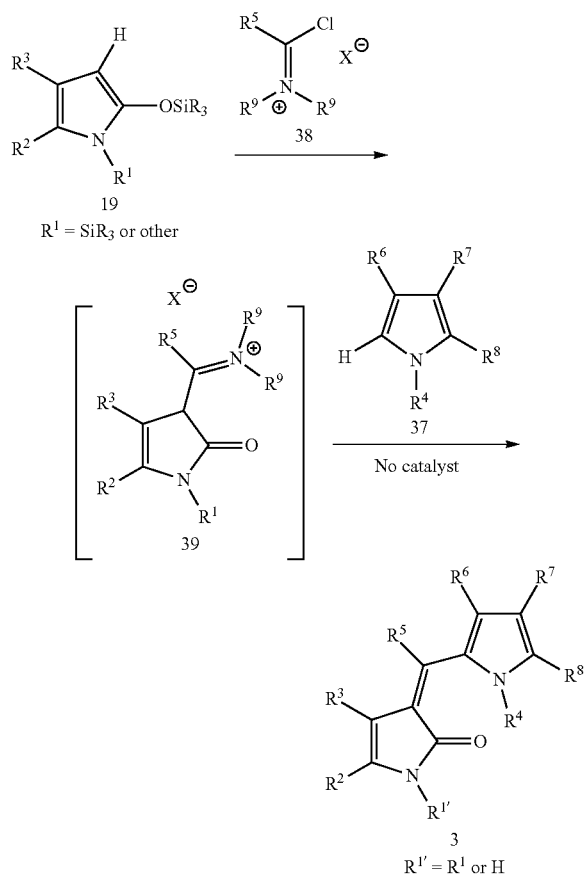

6) Another embodiment involves the simplified and advantageous preparation of a crystalline form of sunitinib and malic acid that is consistent with Form U disclosed in WO2009067686A2.

The Advantage or Characteristics of this Invention

The prior art methods reported for synthesis of the 3-((pyrrol-2-yl)methylene)-2-pyrrolones 3 via the coupling of pyrrolones 4 and 2-formyl-pyrroles 5a units requires the use of bases such as amine bases or alkaline metal alkoxides or carbonates. Some protecting groups and some functional groups are not stable to, or will react with, these bases particularly when more harsh conditions are required and therefore there exists the need for alternative non-basic conditions for the coupling. Moreover, some 2-pyrrolones such as some 2-indolinones have poor solubility requiring the use of polar protic solvents such as alcohols or polar aprotic solvents such as DMF in their coupling reactions with 2-formyl-pyrroles or 2-acyl-pyrroles. Solvents such as DMF can be troublesome on manufacturing scales since they are miscible with water and have high boiling points making it more difficult to recover the reaction product. The use of EtOH can limit the range of substrates because industrial grade EtOH can contaning reactive impurities such as MeOH and water, and is not compatible with compounds possessing non-ethyl esters due to transesterification. Also, often these processes require high reaction temperatures. This invention provides an alternative which comprises the coupling of silylated 2-pyrrolones 19 (i.e., 2-(trisubstituted-silyloxy)-pyrroles), with 2-formyl-pyrroles 5a or 2-acyl-pyrroles 5b in the presence of Lewis acid or Brønsted acids. Under such conditions the acid catalyst allows the coupling reaction to be conducted under more mild conditions and due to enhanced solubility due to silylation in a large range of solvents and at temperature from below ambient temperature (can be used if required due to the instability of the starting materials) or at ambient temperature or higher if required. The use of silylated 2-pyrrolones provides improved solubility and reactivity and they can be useful for reaction of less reactive 2-acyl-pyrroles 5b. The improved solubility of the silylated 2-pyrrolones means a more diverse range of solvents are accessible, and solubility can be modulated by use of different silyl groups. If the 2-formyl-pyrrole 5a or 2-acyl-pyrrole 5b has a free alcohol, amino, amide, urea, carboxylic acid or other protic hetero atomic functional groups, these too can be pre-silylated in situ before the coupling reaction to provide not only protection of the polar protic hetero atomic functional groups, but also to provide better solubility. The silylation and coupling steps can be conducted in a two-step, one-pot mode without isolation of the silylated pyrrolones, or in a two-step, two-pot mode if isolating of the silylated pyrrolones are required for purification purposes (such as by distillation or crystallisation).

This invention can be used to synthesis 3-(pyrrol-2-yl) methylene)-2-pyrrolones 3 with minimal impurity formation as demonstrated in the synthesis of sunitinib which was used to provide high grade sunitinib malate which is a drug substance. The crude sunitinib was so pure that a separate purification step of the crude sunitinib was not required and only a single purification of sunitinib malate by crystallisation was required to obtained material with 99.8% HPLC purity with no individual impurities >0.10% by HPLC. The processes embodied in this invention avoid the use of heavy metal catalysts and chlorinated solvents and are readily applicable to the manufacturing plant scale. The invention has applicability to a range of drug or drug precursors.

EXAMPLES

Example 1

Two-Pot Synthesis of Sunitinib Base

Synthesis of Sunitinib Base:

Under $N_2$, 5-fluoroindolin-2-one (8; 45.6 g, 0.301 mol, 1.0 eq.), $(NH_4)_2SO_4$ (3.96 g, 0.030 mol, 0.1 eq.) and HMDS (437.2 g, 567.8 mL, 2.709 mol, 9.0 eq.) were charged into a flask with a magnetic stirrer and a thermometer at ambient temperature. The mixture was heated with stirring at reflux until the in-process control criterion was passed (7 to 8 h). The mixture was concentrated in vacuo (relative vacuum NLT 0.095 MPa) at about 60° C. until no further distillate was collected. The thus obtained crude 5-fluoro-1-(trimethylsilyl)-2-(trimethylsilyloxy)-1H-indole (20) was obtained and MeCN (1685 g, 2160 mL, 27 P w.r.t. N-(2-(diethylamino)ethyl)-5-formyl-2,4-dimethyl-1H-pyrrole-3-carboxamide (13)) were charged into a 5 L flask with a mechanical stirrer and a thermometer at ambient temperature, the mixture was stirred, and TMSOTf (13.38 g, 10.8 mL, 0.060 mol, 0.2 eq.) was added dropwise into the above mixture. The heterogeneous mixture was heated to reflux, and then a solution of 13 (80.0 g, 0.301 mol, 1.0 eq) in DMF (240 mL, 3 P w.r.t. 13) that was prepared at about 60° C. in advance was added dropwise to the refluxing mixture over a 3 to 4 h period. The reaction mixture was further stirred at reflux until the in-process control criterion was passed (1 to 2 h). The mixture was cooled down to about 25° C., and poured into aqueous saturated NaHCO$_3$ (4 L, 50 P w.r.t. 13) at ambient temperature. The mixture was stirred at ambient temperature for 30 min and at about 0° C. for 2 h, and vacuum filtered at ambient temperature. The filter cake was slurried with water (4 L, 50 P w.r.t. 13) for 10~15 min at ambient temperature, vacuum filtered at ambient temperature, and the filter cake was slurried with EtOH (315 g, 400 mL, 5 P w.r.t. 13) for about 5 min at ambient temperature, vacuum filtered at ambient temperature, and dried in vacuo (relative vacuum NLT 0.095 MPa) at about 40° C. for 30 to 40 h to give 99.8 g of crude sunitinib with 99.2% purity by HPLC analysis and 0.37% by LOD in about 82.4% yield. m.p. 214~216.0° C., $^1$H NMR (DMSO-d$_6$) δ: 0.96~1.01 (t, 6H, J=7.2 Hz, 2*CH$_3$), 2.43 (s. 3H, CH$_3$), 2.45 (s. 3H, CH$_3$), 2.48~2.58 (m, 6H, J=7.2 Hz, 6.9 Hz, 3*CH2), 3.28~3.33 (t, 2H, J=6.9 Hz, CH$_2$), 6.85 (dd, 1H, J=2.1 Hz, 9.4 Hz, 2.7 Hz CH), 6.98 (dd, 1H, J=2.1 Hz, 9.4 Hz, 2.7 Hz CH), 7.50~7.54 (1H, NH), 7.68 (s, 1H, CH), 7.69~7.73 (m, 1H, J=2.1 Hz, 9.4 Hz, CH), 13.62 (s, 1H, NH), $^{13}$C NMR (300 MHz, DMSO-d$_6$) δ: 11.25, 12.53, 13.93, 37.51, 47.15, 52.28, 106.58, 110.63, 115.33, 121.25, 125.40, 126.36, 127.79, 130.80, 135.11, 137.15, 157.34, 160.44, 165.16, 170.13

Synthesis of Sunitinib Malate:

Under N$_2$, crude sunitinib (98.5 g, 0.247 mol, 1.0 eq. 99.2% by HPLC) and MeOH (3113 g, 3940 mL, 40 P w.r.t. crude sunitinib) were charged into a flask with a mechanical stirrer and a thermometer at ambient temperature. The heterogeneous mixture was stirred for 30 min at ambient temperature and L-malic acid (34.8 g, 0.259 mol, 1.05 eq.) was added at about 25° C. The mixture turned clear after 5 to 30 min and was vacuum filtered. The filtrate was stirred for 8 h at about 25° C. The mixture was vacuum filtered at ambient temperature, washed with MeOH (156 g, 197 mL, 2 P w.r.t. crude sunitinib) and dried in vacuo (relative vacuum NLT 0.095 MPa) at about 40° C. for 15 to 18 h to give 118.0 g of crude sunitinib malate with 99.5% purity by HPLC analysis and 0.40% by LOD in 90% yield. m.p. 195.0 to 196.0° C. Under N$_2$, DMSO (506 g, 460 mL, 4 P w.r.t. crude sunitinib malate) was charged into a flask with a mechanical stirrer and a thermometer at ambient temperature and heated to about 45° C. for 5 to 10 min. Crude Sunitinib malate (115 g, 0.216 mol, 1.0 eq.) was charged and DMSO (64 g, 58 mL, 4 P w.r.t. crude sunitinib malate) was used to assist the transformation and after 5 to 10 min the mixture almost turn clear and was vacuum filtered. MIBK (1104 g, 1380 mL, 12 P w.r.t. crude sunitinib malate) was charged into the flask, and the solution was allowed to cool about 20° C. and was stirred for a further 30 h at about 20° C. The mixture was vacuum filtered and washed with MIBK (368 g, 460 mL, 4 P w.r.t crude sunitinib malate) and dried in vacuo (relative vacuum NLT 0.095 MPa) at about 40° C. for 30 to 40 h to give 98.1 g of pure sunitinib malate as a yellow powder with 99.8% purity by HPLC analysis and 0.27% by LOD in 85.3% yield. No individual impurities were present at greater than 0.10% by HPLC analysis. $^1$H NMR (300 MHz, DMSO-d$_6$) δ: 0.98 (t, 6H, J=7.2 Hz, CH$_3$), 2.31~2.38 (dd,1H, J=5.8 Hz, 15.75 Hz, CH$_2$), 2.43, 2.45 (s. 6H, CH$_3$), 2.56~2.62 (m, 1H, CH2), 3.03~3.12 (m, 6H, 3*CH$_2$), 3.51~3.55 (t, 3H, CH$_2$), 3.95~3.99 (dd, 1H, CH).

Example 2

One-Pot Synthesis of Sunitinib Base

A 25 mL single neck flask was charged with 0.57 g (1.0 eq) of 8, 0.05 g (0.1 eq) of (NH$_4$)$_2$SO$_4$ and 7.1 mL (9 eq.) of HMDS. The mixture was heated to reflux for 5 h to give a clear solution, then MeCN (21 mL) and 13 (0.93 g, 1.0 eq) were added followed by TMSOTf (127 μl, 0.2 eq) added dropwise over 0.5 min. The reaction mixture was heated to reflux for 29.3 h and was then cooled to room temperature and poured in to 50 mL saturated NaHCO$_3$ solution. The slurry was stirred in an ice bath for 2 h and then filtered. The filter cake was washed with 50 mL water and then dried at 40° C. under vacuum for 8 hrs to give a yellow solid (1.24 g, 92.2% purity by HPLC) in 82% yield.

Example 3

Two-Pot Synthesis of Sunitinib Base with 1 eq. of TMSOTf

A 25 mL single neck flask was charged with 0.57 g (1.0 eq) of 8, 0.05 g (0.1 eq) of (NH$_4$)$_2$SO$_4$ and 7.1 mL (9 eq.) of HMDS. The mixture was heated to reflux for 5 hrs to give a clear solution, which was distilled at 60° C. under vacuum to remove the HMDS. The distillation residue, MeCN (28 mL, 30 P) and 13 (0.93 g, 1.0 eq) were added to a 50 mL three neck flask. Then TMSOTf (636 μl, 1.0 eq) was added dropwise over 0.5 min and the reaction mixture was heated to 45° C. for 4.9 h to pass the coupling in-process control criterion. The reaction mixture was cooled to room temperature and poured into 50 mL saturated NaHCO$_3$ solution. The slurry was stirred in an ice bath for 2 h then filtered. Filter cake was washed with 50 mL water and then dried at 40° C. under vacuum for 8 h to give a yellow solid (1.19 g, 95.0 purity by HPLC) in 81% yield.

Example 4

Two-Pot Synthesis of Sunitinib Base Using THF

A 25 mL single neck flask was charged with 0.57 g (1.0 eq) of 8, 0.05 g (0.1 eq) of (NH$_4$)$_2$SO$_4$ and 7.1 mL (9 eq.) of HMDS. The mixture was heated to reflux for 5 h to give a clear solution, which was distilled at 60° C. under vacuum to remove HMDS. The distillation residue, THF (28 mL, 30 P) and 13 (0.93 g, 1.0 eq) were added to a 50 mL three neck flask. Then TMSOTf (127 μl, 0.2 eq.) was added dropwise over 0.5 min and the reaction mixture was heated to reflux for 30.7 h to pass the coupling in-process control criterion. The reaction mixture was cooled to room temperature and poured into 50 mL saturated NaHCO$_3$ solution. The slurry was stirred in an ice bath for 2 h then filtered. The filter cake was washed with 50 mL water and then dried at 40° C. under vacuum for 8 h to give a yellow solid (1.16 g, 92.6% purity by HPLC) in 77% yield.

Example 5

One-Pot Synthesis of Sunitinib Base Using BSTFA

Under N$_2$, 5-fluoroindolin-2-one (8, 2.0 g, 13.2 mmol, 1.0 eq.), MeCN (60 mL, 3 P) and BSTFA (10.22 g, 39.6 mmol, 3.0 eq.) were charged into a flask with a magnetic stirrer and a thermometer at ambient temperature. The mixture was heated with stirring at reflux until the in-process control criterion passed (about 5 h). To the thus prepared 20 was added 13 ((3.58 g, 1.0 eq.) and TMSOTf (0.67 mL, 0.3 eq.). The mixture was heated at reflux for 18 h. The mixture was cooled down to r.t., and poured into water (60 mL) and stirred for 13 h. The mixture was vacuum filtered, and the filter cake was washed with water and then with EtOH and dried in vacuo to give 3.43 g of crude sunitinib with 99.4% purity by HPLC analysis in 73% yield.

Example 6

One-Pot Synthesis of Sunitinib Base Using BSTFA 13 (3.51 g, 1.0 eq.), MeCN (40 mL) and TMSOTf (0.45 mL, 0.2 eq.) were charged into a flask with a mechanical stirrer and a thermometer at ambient temperature. The heterogeneous mixture was heated to reflux, 20 (1.0 eq.) was dropped at reflux over 1 h, and the reaction mixture was further stirred at reflux over period of 5 h. The mixture was cooled down to r.t., 10 mL water was added, stirred, filtered, washed with ethanol, filter cake was dried in vacuo to give 2.35 g of crude sunitinib with 98.3% purity by HPLC analysis in 70% yield.

Example 7

One-Pot Synthesis of Sunitinib Base Using BSTFA No Catalyst or with Using $Et_3N$ 20 (1.0 eq.) in BSTFA/MeCN (as prepared in Example 5) and 13 (3.51 g, 1.0 eq.) were charged into a flask with a mechanical stirrer and a thermometer at ambient temperature. The reaction mixture was further stirred without any catalyst at reflux over period of 36 h. The mixture was cooled down to r.t., and adjusted pH to 3~4 with aq. HCl, filtered, pH of filtrate was adjusted to 9~10 with aq. NaOH, filtered, wash with $H_2O$ and then with EtOH. The filter cake was dried in vacuo to give 2.35 g of crude sunitinib with 95.3% purity by HPLC analysis in 43% yield. When this experiment was repeated with the addition of $Et_3N$ (0.2 eq.) to the 20 and 13 2.9 g of crude sunitinib with 89% purity by HPLC analysis in 49% yield was obtained after 37 h at reflux.

Example 8

One-Pot Synthesis of Sunitinib Base Using BSTFA 20 (1.0 eq.) in BSTFA/MeCN (as prepared in Example 5) and 13 (14.04 g, 1.0 eq.) were charged into a flask with a mechanical stirrer and a thermometer at ambient temperature, the mixture was stirred, and TMSOTf (2.68 mL, 0.3 eq.) was added into the above mixture. The heterogeneous mixture was heated at reflux for 17 h. The mixture was cooled down to r.t. To a 50 mL sample from the reaction mixture was added 80 mL water, and the mixture was stirred, filter, and the filter cake was dried in vacuo to give 1.69 g of crude sunitinib with 95.0% purity by HPLC analysis in 37% yield. To an identical 50 mL sample was added 80 mL sat. $NaHCO_3$, and the mixture was stirred, filter and washed with water; The filter cake was dried in vacuo to give 1.89 g of crude sunitinib with 88.9% purity by HPLC analysis in 38% yield. To another identical 50 mL sample was added $3HF.Et_3N$ (16.73 g), and the mixture was stirred, filter and washed with water. The filter cake was dried in vacuo to give 1.36 g of crude sunitinib with 95.4% purity by HPLC analysis in 30% yield.

In a similar way to a 23 mL sample for a similar reaction was added i-PrOH (5 mL), and the mixture was stirred, and filtered. The filter cake was dried in vacuo to give 0.55 g of crude sunitinib with 98.7% purity by HPLC analysis in 41% yield. To another 23 mL sample was added n-BuOH (5 mL), and the mixture was stirred, and filter. The filter cake was dried in vacuo to give 0.72 g of crude sunitinib with 98.4% purity by HPLC analysis in 53% yield. To another 23 ml sample was added 30% $MeNH_2$ in water (5 mL), and the mixture was stirred, and filter. The filter cake was dried in vacuo to give 1.28 g of crude sunitinib with 97.9% purity by HPLC analysis in 87% yield.

Example 9

One-Pot Synthesis of Sunitinib Base Using BSTFA and THF 20 (1.0 eq.) in BSTFA/THF (as in example 5 except used THF instead of MeCN) in THF (240 mL), 13 (14.04 g, 1.0 eq.) and TMSOTf (2.68 mL, 0.3 eq.) were charged into a flask with a mechanical stirrer and a thermometer below 50° C. The heterogeneous mixture was heated to 50~65° C., the reaction mixture was further stirred at 50~65° C. over period of 46 h. The mixture was cooled down to r.t., filtered, washed with THF, filter cake was dried in vacuo to give 17.05 g of crude sunitinib with 97.0% purity by HPLC analysis in 78.5% yield

Example 10

Two-Pot Synthesis of Sunitinib Base Using TsOH or $H_2SO_4$ or Malic Acid

A 25 mL single neck flask was charged with 0.57 g (1.0 eq) of 8, 0.05 g (0.1 eq) of $(NH_4)_2SO_4$ and 15.7 mL (20 eq.) of HMDS. The mixture was heated to reflux for 7.5 h to give a clear solution, which was distilled at 60° C. under vacuum to remove HMDS. The distillation residue, MeCN (20 mL, 14.2 P) and 13 (0.94 g, 1.0 eq) were added to a 50 mL three neck flask. Then TFA (0.2 eq.) or TsOH (0.12 g, 0.2 eq) or $H_2SO_4$ (38 µl, 0.2 eq) or malic acid (1.0 eq.) was added and the reaction mixture was stirred at 25° C. for 18.3 h or 24 h or 44 h or 21.4 h, respectively, to pass the coupling in-process control criterion. In the case of malic acid, the reaction mixture was then heated to reflux for 52 h. Apart for the malic acid reaction, the reaction mixture was poured into 30 mL saturated $NaHCO_3$ solution. The slurry was stirred in an ice bath for 2 h then filtered. Filter cake was washed with 30 mL water and then dried at 40° C. under vacuum for 8 h to give a yellow solid (0.91 g, 97.5% purity by HPLC in 72% yield for TFA catalysis, or 1.13 g, 97.1% purity by HPLC in 77.7% yield for $H_2SO_4$ catalysis or 1.09 g, 93.8% purity by HPLC in 72% yield for TsOH). In the malic acid case the product as cooled to room temperature and filtered. The filter cake was dried at 40° C. under vacuum for 8 h to give a yellow solid (1.40 g, 92.6% purity by HPLC in 57.7% yield).

Example 11

Direct Isolation of Sunitinib Malate from Coupling Reaction 13 (3.0 g), MeCN (35 mL) and TMSOTf (0.38 mL, 0.2 eq.) were charged into a flask with a mechanical stirrer and a thermometer at ambient temperature. The heterogeneous mixture was heated to reflux, 20 (prepared as in example 5; 1.0 eq.) in MeCN (35 mL) was dropped at reflux over 1 h, and the reaction mixture was further stirred at reflux over period of 12 h. The mixture was cooled down to r.t., malic acid (3.03 g, 2.0 eq.) in MeOH (23 mL) was added into above reaction mixture. The reaction mixture turned clear. After 2 h, some solid appeared; after 22 h, filtered, washed with MeOH (10 ml). Filter cake was dried in vacuo to give 4.2 g of crude sunitinib malate with 97.3% purity by HPLC analysis in 70.0% yield.

Example 12

Direct Isolation of Sunitinib as a MsOH, Tartaric Acid, Frifluoroacetic Acid, CSA, AcOH, BzOH, HCl, or HBr Salt from the Coupling Reaction 13 (5.3 g), MeCN (60 mL) and TMSOTf (1.01 mL, 0.3 eq.) were charged into a flask with a mechanical stirrer and a thermometer at ambient temperature. The heterogeneous mixture was heated to reflux, 20 (prepared as in example 5; 1.0 eq.) in MeCN (60 mL) was dropped at reflux over 1.5 h, and the reaction mixture was further stirred at reflux over period of 8 h. The mixture was divided up and treated as follows:

A 23 mL sample from above, MsOH (0.64 g, 2 eq.) in MeOH (4 mL) was added at r.t. The reaction mixture turned clear. After 16 h the mixture was filtered, washed with MeOH and the filter cake was dried in vacuo to give 1.38 g of crude sunitinib mesylate salt with 98.4% purity by HPLC analysis in 68.9% yield.

A 23 mL sample from above, tartaric acid (1.0 g, 2 eq.) in MeOH (4 mL) was added at r.t. The reaction mixture turned clear. After 15 h, filtered, washed with MeOH and the filter cake was dried in vacuo to give 1.06 g of crude sunitinib tartrate salt with 97.4% purity by HPLC analysis in 56.5% yield.

A 23 mL sample from above, TFA (0.76 g, 2 eq.) in MeOH (4 mL) was added at r.t. The reaction mixture turned clear. After 16 h, no solid had appeared so some solvent was removed by evaporated, and the mixture was cooled in an ice-water bath for 2 h, filtered, and washed with MeOH. The filter cake was dried in vacuo to give 0.62 g of crude sunitinib trifluoroacetate with 98.6% purity by HPLC analysis in 35.8% yield.

A 23 mL sample from above, camphorsulfonic acid (1.55 g, 2 eq.) in MeOH (4 mL) was added in r.t. The reaction mixture turned clear. After 15 h, the mixture was filtered, washed with MeOH and the filter cake was dried in vacuo to give 1.39 g of crude sunitinib camphorsulfonate with 98.6% purity by HPLC analysis in 65.2% yield.

A 23 mL sample from a similar reaction as above, AcOH (0.44 g, 2 eq.) in MeOH (4 mL) was added at r.t. The reaction mixture turned clear soon. After 24 h the mixture was filtered, washed with MeOH and the filter cake was dried in vacuo to give 0.7 g of crude sunitinib acetate with 98.5% purity by HPLC analysis in 41.5% yield.

A 23 mL sample from a similar reaction as above, benzoic acid (0.89 g, 2 eq.) in MeOH (4 mL) was added at r.t. The reaction mixture turned clear. After 2 h no solids had appeared, so the solvent was evaporated until a slurry was formed which was filtered and was washed with MeOH. The filter cake was dried in vacuo to give 0.29 g of crude sunitinib benzoate with 98.3% purity by HPLC analysis in 15.2% yield.

A 35 mL from a similar reaction as above was evaporated, MeOH (45 mL) and HCl (0.34 g 2.0 eq.) in MeOH was added at r.t. The reaction mixture turned clear. After 20 h, the mixture was concentrated and then filtered. The filter cake was washed with MeOH and dried in vacuo to give 1.58 g of crude sunitinib hydrochloride with 98.6% purity by HPLC analysis in 76.7% yield.

A 40 mL sample from a similar reaction as above was concentrated under vacuum and MeOH (70 mL) and malic acid (1.59 g, 2 eq.) were added at r.t. The reaction mixture turned clear soon. After 24 h the mixture was concentrated, and n-BuOH (30 mL) was added, and after 16 h the mixture was filtered. The filter cake was washed with MeOH and dried in vacuo to give 2.29 g of crude sunitinib malate with 98.9% purity by HPLC analysis in 71.8% yield.

A 35 mL sample from a similar reaction as above was concentrated under vacuum and MeOH (45 mL) and HBr (0.75 g 2.0 eq.) in MeOH were added at r.t. The reaction mixture turned clear. After 20 h the mixture was concentrated and the mixture was filtered. The filter cake was washed with MeOH and dried in vacuo to give 1.96 g of crude sunitinib hydrobromide with 97.6% purity by HPLC analysis in 86% yield.

Example 13

Free Basing of Sunitinib Salts

Sunitinib methanesulfonate (1.0 g) and $H_2O$ (60 mL) was added into a flask in r.t. and heated to 80° C., the mixture turned clear. The pH of the mixture was adjusted to 8~9 with 1N NaOH and cooled r.t., was stirred overnight, filtered, washed, and dried in vacuo to give 0.65 g of crude sunitinib with 99.2% purity by HPLC analysis in 99.5% yield.

Sunitinib hydrochloride (1.0 g) and $H_2O$ (60 mL) was added into a flask in r.t. and heated to 90° C., the mixture turned clear, pH of the mixture was adjusted to 8~9 with 1N NaOH and cooled r.t. stirred over night, filtered, washed, dried in vacuo to give 0.67 g of crude sunitinib with 99.0% purity by HPLC analysis in 78.3% yield.

Example 14

A 25 mL single neck flask was charged with 8 (1.14 g, 1.0 eq), $(NH_4)_2SO_4$ (0.10 g, 0.1 eq) and of HMDS (14.1 mL, 9 eq). The mixture was heated to reflux for 7 h to give a clear solution, which was then distilled at 60° C. under vacuum to remove HMDS. The distillation residue and MeCN (44 mL, 22 P) were added in to a 100 mL three-neck flask. After TMSOTf (2.74 mL, 2.0 eq) diluted with MeCN (10 mL, 5 P) was added dropwise over approximately 30 seconds, a solution of 13 (2.0 g, 1 eq.) in DMF (6 mL, 3 P) was added dropwise over a 3 h period. The reaction mixture was allowed to keep stirring at r.t. over night. The reaction mixture was poured into saturated $NaHCO_3$ solution (100 mL) and was stirred at r.t. for 0.5 h and then was cooled in an bath for 2 h. The slurry was filtered and the filter cake was washed with water (100 mL) and then dried at 40° C. under vacuum for 8 h to give the Sunitinib as a yellow solid (2.80 g, 97.1% purity by HPLC) in 90.5% yield.

Example 15

Synthesis of (Z)-5-((5-fluoro-2-oxoindolin-3-ylidene)methyl)-2,4-dimethyl-1H-pyrrole-3-carboxylic acid (15) using TMSOTf $(NH_4)_2SO_4$ (0.05 g, 0.38 mmol) was added into a stirred mixture of 8 (0.57 g, 3.77 mmol) in HMDS (7.1 mL, 12.5 P.) at room temperature. The reaction mixture was then heated to reflux and maintained at that temperature for no less than 5 hours. Monitor the reaction by GC. After the reaction is completed, the reaction was distilled to remove about half of HMDS to give 20 of about 90% GC purity. To the solution of 20 in HMDS (about 3.5 mL, 6.25 P.) at 45° C. was added MeCN (30 mL, 52.6 P.). After stirring for 15 minutes, 5-formyl-2,4-dimethyl-1H-pyrrole-3-carboxylic acid (14; 0.63 g, 3.77 mmol) and TMSOTf (0.16 g, 0.72 mmol) were added. Then the mixture was stirred for more than 4 hours, once the reaction was complete (as indicated by HPLC analysis) it was quenched with water (3 mL, 5 P.). The mixture was filtered and the filtrate cake was washed with Ethanol (5 mL), then it was dried under vacuum at 40° C. overnight to give the goal product 15 (1.03 g, 91% yield) as a yellow to brown powder with about 85% HPLC purity. $^1$H NMR (300 MHz, d$_6$-DMSO): δ 2.48 (m, 6H, H-20, 21), 6.83 (m, 1H, H-6), 6.85 (m, 1H, H-4), 7.71 (m, 1H, H-12), 7.73 (m, 1H, H-1), 10.98 (s, 1H, H-7), 13.95 (s, 1H, H-14). API-ESI (NEG): m/z 299.0

Example 16

Synthesis of 15 Using TfOH

To a solution of 20 (prepared as in Example 16 from 5 g of 8) in HMDS (about 75 mL, 15 P) at r.t. was added MeCN (50 mL, 10 P). After stirring for 15 minutes, 14 (5.55 g, 33.1 mmol) and TfOH (0.5 g, 3.3 mmol) were added. Then the mixture was stirred for 24 hours, the reaction was heated to 65° C. for another 24 hours, once the reaction was complete (as indicated by HPLC analysis) it was quenched with water (3 mL). The mixture was filtrated and the filtrate cake was dried under vacuum at 40° C. overnight to give the goal product 15 (9.7 g, 97% yield) as a yellow to brown powder with about 88.9% HPLC purity.

Example 17

Synthesis of 15 Using TMSOTf in One-Pot (NH$_4$)$_2$SO$_4$ (0.09 g, 0.67 mmol) was added into a stirred mixture of 8 (1.0 g, 6.61 mmol) in HMDS (20 mL, 20 P) at room temperature. The reaction mixture was then heated to reflux and maintained at that temperature for no less than 5 hours. Monitor the reaction by GC. After the reaction is completed, 14 (1.1 g, 3.77 mmol) and TMSOTf (0.29 g, 1.32 mmol) were added. Then the mixture was stirred, once the reaction was complete (as indicated by HPLC analysis) it was quenched with water (6 mL, 6 P.) and MeCN (30 mL). The mixture was filtrated and the filtrate cake was washed with MeCN (20 mL) and EtOH (5 mL), then it was dried under vacuum at 40° C. overnight to give the goal product 15 (1.92 g, 97% yield) as a yellow to brown powder with about 82.1% HPLC purity.

Example 18

Synthesis of Sunitinib from 15

15 (10 g, 33.3 mmol) was suspended in DMF (50 ml, 5 P.) and stirred for 5 minutes. DIPEA (9.0 mL, 54.5 mmol) was then added and the mixture was stirred for 10 minutes. HATU (13.95 g, 36.7 mmol) was added and the reaction mixture was stirred at 25° C. for completion. HPLC was applied to detect the completion of the reaction. Most of the DMF was removed by rotary evaporating and the residue was suspended in MeCN (100 mL, 10 P.) and stirred for another 1 hour. The solid was collected by filtration, washed with MeCN, and dried under vacuum at 40° C. overnight. The intermediate (Z)-3H-[1,2,3]triazolo[4,5-b]pyridin-3-yl 5-((5-fluoro-2-oxoindolin-3-ylidene)methyl)-2,4-dimethyl-1H-pyrrole-3-carboxylate (15b) (12 g, 86.5 percent yield) with 86.8% HPLC purity as a yellow powder was got. $^1$H NMR (300 MHz, DMSO-d$_6$): δ 2.61 (s, 3H, H-31), 2.68 (s, 3H, H-16), 6.87 (m, 1H, H-2), 7.01 (m, 1H, H-6), 7.64 (m, 1H, H-10), 7.85 (m, 1H, H-3), 8.73 (dd, J=1.5, 1.2 Hz, 1H, H-28), 8.83 (dd, J=1.2, 1.5 Hz, 1H, H-27), 13.11 (s, 1H, NH). To a 15b (10.0 g, 23.9 mmol) DMF solution was added N,N-diethylethane-1,2-diamine (7; 3.33 g, 28.7 mmol), the reaction mixture was stirred at 25° C. for completion. HPLC was applied to detect the completion of the reaction. Most of the DMF was removed by rotary evaporating and the residue was suspended in MeCN (100 mL, 10 P.) and stirred for another 1 hour. The solid was collected by filtration, washed with MeCN, and dried under vacuum at 40° C. overnight to give Sunitinib (8.38 g, 88% yield) with 77.6% HPLC purity.

Example 19

Synthesis of Sunitinib New Malate Salt Form

Figure 10:
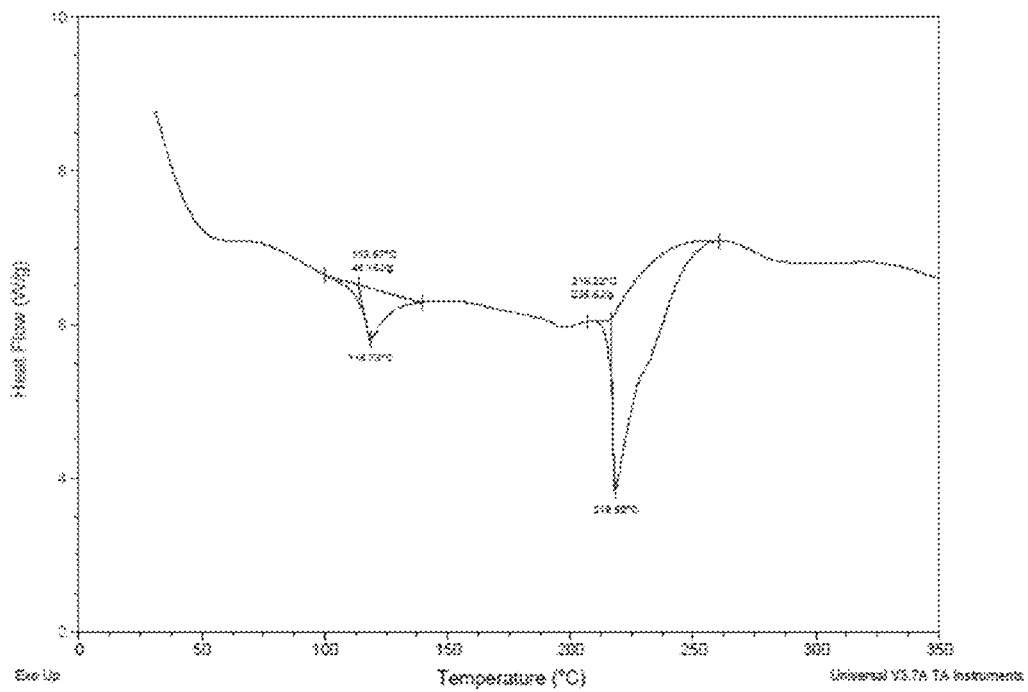
FIG. 10—shows the Differential Scanning Calorimetry of the product made in Example 19.

A DMSO (440 mL, 4.50 P, water content by Karl Fischer titration 907 ppm H$_2$O) solution was pre-heated to 45° C. Sunitinib malate (98.0 g, 99.7% HPLC purity, m.p. 191° C., LOD 0.32%) was charged and the mixture was stirred for 20 min at 45° C. and then filtered. To the filtrate at 45° C. was added MIBK (1180 mL, 12 P, water content by Karl Fischer titration 2018 ppm H$_2$O). The mixture was cooled to r.t and stirred for about 62 h. The mixture was filtrated and the cake was washed with MIBK (390 mL, 4.0 P, water content by Karl Fischer analysis 2018 ppm), then it was dried under vacuum at 40° C. overnight to give the product malate salt form (71.6 g, 73% yield) as an orange to red powder with 99.70% purity by HPLC analysis. LOD 11.5%; m.p. 171° C.~191° C. The XRPD pattern and DSC traces are shown in FIGS. 9 and 10, respectively.

Recrystallisation of Sunitinib New Malate Salt Form

DMSO (22.5 mL, 4.50 P, water content by Karl Fischer titration 332 ppm H$_2$O) was pre-heated to 45° C. and Sunitinib new malate salt form (5.0 g, 99.7% purity by HPLC analysis from above step) was added and was stirred for 5 min at 45° C. MIBK (60 mL, 12 P, water content by Karl Fischer titration 76 ppm H$_2$O) was charge at 45° C. and the mixture was cooled to 20° C. and was stirred for about 30 h. The mixture was filtered and the filter cake was washed with MIBK (20 mL, 4.0 P, water content by Karl Fischer analysis 97 ppm), then was dried under vacuum at 40° C. overnight to give an orange to red powder (3.70 g, 74% yield) with about 99.8% purity by HPLC analysis. LOD 0.43%; m.p. 215° C.~216° C.

Example 20

Synthesis of a Sunitinib New Malate Salt Form

A mixture of DMSO (22.5 mL, 4.50 P, water content by Karl Fischer analysis 303 ppm) and water (0.1 mL, 0.02 P, 0.6 eq.) was pre-heated to 55° C. and Sunitinib malate (5.0 g, 99.48% purity by HPLC analysis, 1.0 eq.) was charged into the solvent and stirred for 25 min at 55° C. Then a mixture of MIBK (60 mL, 12 P, water content by Karl Fischer analysis 76 ppm) and water (0.1 mL, 0.02 P, 0.6 eq.) was charge at 55° C. The mixture was cooled to 20° C. and further stirred for about 30 h. The mixture was filtered and the cake was washed with MIBK (20 mL, 4.0 P, water content by Karl Fischer analysis 76 ppm), then was dried under vacuum at 40° C. overnight to give a sunitinib new malate salt form (3.70 g, 74.0% yield) as an orange to red powder with about 99.58% purity by HPLC analysis. m.p. 213° C.~216° C.

Example 21

Preparing a Sunitinib Analogue 17 by Vilsmeier Salt and (2,4-dimethyl)-1H-pyrrole-3-carboxylic acid ethyl ester (40)

A mixture of 8 (1.14 g, 1.0 eq), (NH4)$_2$SO$_4$ (0.10 g, 0.1 eq.) and 14.1 mL (9 eq.) of HMDS was heated to reflux for 7 h to give a clear solution, which was distilled at 60° C. under vacuum to remove HMDS providing 20. To the ice cooled mixture of DMF (3.07 g) and DCM (50 mL) was slowly added oxalyl chloride (5.23 mL). A white slurry formed and which was stirred in an ice bath for 40 min. The DCM was evaporated at r.t. under reduced pressure to give a semi-solid which was dried at 60° C. in vacuo for 30 min to give the Vilsmeier salt 41 as a white powder. To a slurry of the Vilsmeier salt (1.1 g) 41 and MeCN (10.8 mL) was added (2,4-dimethyl)-1H-pyrrole-3-carboxylic acid ethyl ester (40) in MeCN (14.9 mL) dropwise over a 20 min period providing a clear red-brown solution followed by the precipitation of a white solid. The resultant slurry was stirred at r.t. for 40 min and then 20 was added into the reaction mixture providing a clear dark red-brown coloured solution. After about five minutes a yellow solid precipitated which was stirred at r.t. for a further 2.5 h. The reaction product was collected by filtration and the filter cake was washed three times with MeCN (5 mL each) and dried under vacuum to give 1.05 g (40%) of (Z)-ethyl 5-((5-fluoro-2-oxoindolin-3-ylidene)methyl)-2,4-dimethyl-1H-pyrrole-3-carboxylate (17) as a yellow solid with 93.4% HPLC purity. $^1$H NMR (300 MHz, DMSO-d$_6$) δ 13.84 (s, 1H, H17), 10.91 (s, 1H, H7), 7.72, (dd, J=9.4, 2.5 Hz, 1H, H3), 7.67 (s, 1H, H10), 6.93-6.87 (m, 1H, H6), 6.79 (dd, J=8.5, 4.6 Hz, 1H, H2), 4.14 (q, J=7.1 Hz, 2H, H22), 2.47 (s, 3H, H24), 2.44 (s, 3H, H25), 1.24 (t, J=7.1 Hz, 3H, H23); $^{13}$C NMR (300 MHz, DMSO-d$_6$) δ 170 (C8), 164 (C19) 159 (C1), 141 (C4), 135 (C13), 133 (C11), 127 (C5), 126 (C3), 125 (C10), 116 (C15), 114 (C9), 113 (C6), 110 (C14), 107 (C2), 59 (C22), 16(C24), 14(C25), 12 (C23); ESI-MS (Positive mode): 329 ([MH]$^+$, 67%); ESI-MS (Negative mode): 327 ([M-H]$^+$, 100%).

Example 22

Preparing a Sunitinib Analogue 44 by Coupling of 2-acetyl pyrrole (43) and 20

A mixture of 8 (1.14 g, 1.0 eq), (NH4)$_2$SO$_4$ (0.10 g, 0.1 eq.) and 14.1 mL (9 eq.) of HMDS was heated to reflux for 7 h to give a clear solution, which was distilled at 60° C. under vacuum to remove HMDS providing 20. To a solution of the above prepared 20 (1 eq.) in MeCN (10 mL) was added TMSOTf (685 μL, 0.5 eq.) followed by a solution of 2-acetyl pyrrole (43; 0.82 g, 1 eq.) in MeCN (10 mL) dropwise at r.t. The mixture was stirred at 45° C. for 1.5 h, and then at reflux for 0.5 h. A solution of 43 (0.82 g, 1 eq.) in MeCN (4 mL) was added dropwise and stirred for about another 2 hours. The precipitated solid was filtered and washed with MeCN (2 mL) and dried under vacuum giving a brown-yellow solid (0.30 g) with 92% HPLC purity. $^1$H NMR (300 MHz, DMSO-d$_6$) δ 11.03 (s, 1H, H17), 7.51 (dd, J=11.0, 2,4 Hz, 1H, H13), 7.38 (dd, J=2.2, 1.3 Hz, 1H, H3), 7.13 (dd, J=3.9, 1.2 Hz, 1H, H6), 7.01 (td, J=9.0, 2.5 Hz, 1H, H2), 6.89 (dd, J=8.5, 5.0 Hz, 1H, H15), 6.39 (dd, J=3.9, 2.4 Hz, 1H, H14), 3.40 (s, 1H, H7), 2.75 (s, 3H, CH$_{16}$); ESI-MS (Positive mode): 243: ([MH]$^+$, 100%); ESI-MS (Negative mode): 241 ([M-H]$^+$, 100%).

The invention claimed is:
1. A process for preparing a substituted 3-((pyrrol-2-yl) methylene)-2-pyrrolone of formula (I) or a salt thereof:

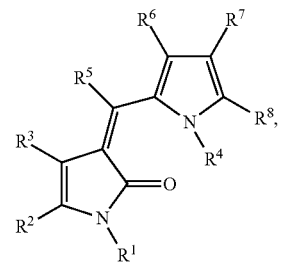

(I)

comprising:
a) reacting a compound of formula (II):

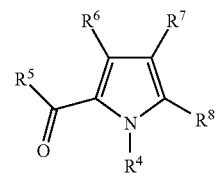

(II)

or a compound of formula (V):

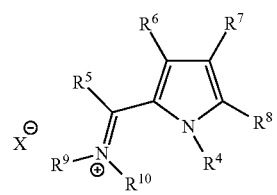

(V)

with a compound of formula (III):

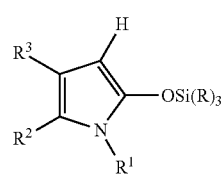

(III)

to obtain the substituted 3-((pyrrol-2-yl)methylene)-2-pyrrolone of formula (I), wherein $R^1$ and $R^4$ are optionally and independently H, $C_1$-$C_8$ alkyl, aryl, benzyl, heteroaryl, silyl; $R^2$ and $R^3$ are optionally and independently H, $C_1$-$C_8$ alkyl, aryl, heteroaryl, or together form a substituted or unsubstituted ring; R independently is $C_1$-$C_8$ alkyl, aryl, H or an oxygen-based substituent; $R^5$ is H, $C_1$-$C_8$ alkyl, aryl, heteroaryl, or COR' wherein R' is H, $C_1$-$C_8$ alkyl, aryl, heteroaryl, O—$C_1$-$C_8$ alkyl, N,N-di-$C_1$-$C_8$ alkyl, NH—$C_1$-$C_8$ alkyl or N, N-diaryl; $R^6$, $R^7$, and $R^8$ independently are H, $C_1$-$C_8$ alkyl, aryl, heteroaryl, silyl, COR" wherein R" is H, $C_1$-$C_8$ alkyl, aryl, benzyl, heteroaryl, substituted or unsubstituted heterocyclic, OH, SH, NH$_2$, O—C$_1$-C$_8$ alkyl, NH—C$_1$-C$_{12}$ alkyl, N,N-di-C$_1$-C$_{12}$ alkyl, N,N-diaryl, N,N-dibenzyl, or S—C$_1$-C$_8$ alkyl; and optionally where R$^5$ and R$^6$ together form a ring; and optionally where R$^6$ and R$^7$ together form a ring; and optionally where R$^7$ and R$^8$ together form a substituted or unsubstituted ring, and R$^9$ and R$^{10}$ are independently selected from C$_1$-C$_{12}$ alkyl or silyl, or in the alternative, R$^9$ and R$^{10}$ form a ring together; X is Cl, Br, I, triflate (OTf), OP(O)Cl$_2$ OP(O)Br$_2$ OH, tosylate (TsO), mesylate (MsO), or R'''CO$_2$, where R''' is C$_1$-C$_8$ alkyl, aryl or heteroaryl; and b) optionally reacting the substituted 3-((pyrrol-2-yl)methylene)-2-pyrrolone of formula (I) with a salt forming agent to obtain the salt thereof;

wherein the reaction between the compound of formula (II) and the compound of formula (III) in the reacting step a) is conducted in the presence of a catalyst and in a solvent.

2. The process according to claim 1 wherein the substituted 3-((pyrrol-2-yl)methylene)-2-pyrrolone of formula (I) is selected from the following compounds:

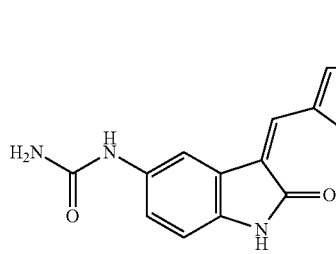

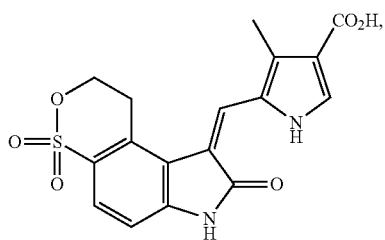

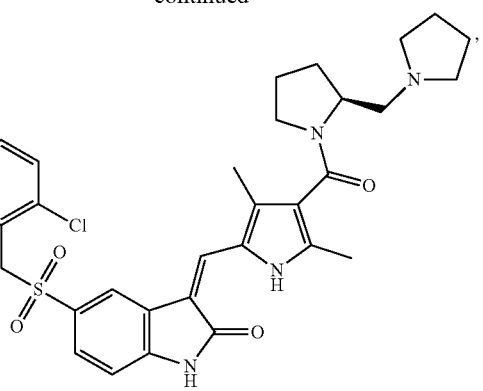

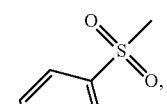

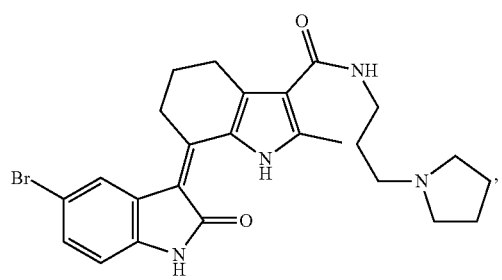

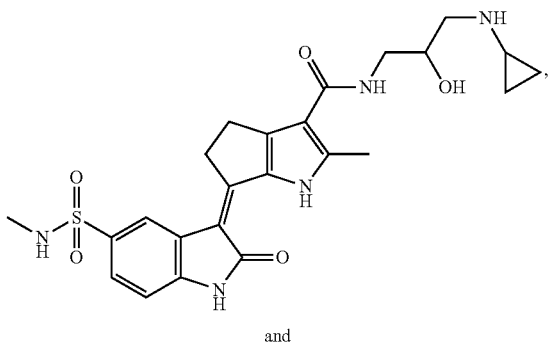

and

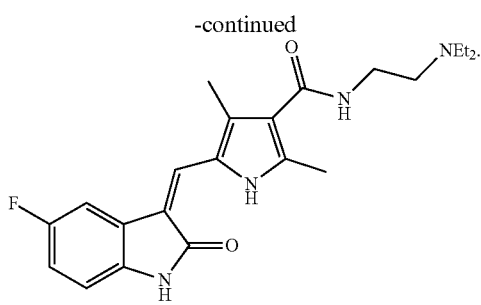

3. The process of claim 1, wherein the catalyst is a Lewis acid or Brønsted acid catalyst.

4. The process of claim 3 where the Lewis acid is selected from the group consisting of trimethylsilyl trifluoromethanesulfonate (TMSOTf), tert-butyldimethylsilyl trifluoromethanesulfonate (TBSOTf), trimethylsilyl methanesulfonate (TMSOMs), $BF_3 \cdot Et_2O$, $SnCl_4$, $LiClO_4$, $M(OTf)_3$ (where OTf is triflate and M is a lanthanide ion, or Bi), $M(OTf)_4$ (where OTf is triflate and M is a transition metal ion), $ZnCl_2$, $ZnBr_2$, $ZnI_2$, $AlCl_3$, $MgCl_2$, $MgBr_2$ and $TiCl_4$.

5. The process of claim 4, wherein the Lewis acid catalyst is trimethylsilyl trifluoromethanesulfonate (TMSOTf).

6. The process of claim 3, wherein the Brønsted acid is selected from the group consisting of carboxylic acids and halocarboxylic acids.

7. The process of claim 5, wherein the molar percentage of trimethylsilyl trifluoromethanesulfonate (TMSOTf) is 5 mol % to 200 mol % with respect to the compound of formula (II).

8. The process of claim 1 further comprising silylating a compound of formula (IV) with a silylating agent:

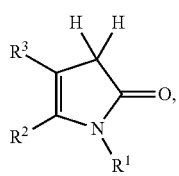

wherein $R^1$, $R^2$ and $R^3$ are defined in claim 1 to obtain the compound of formula (III).

9. The process of claim 8, wherein the silylating agent is selected from the group consisting of hexamethyldisilazane (HMDS), N,O-bis(trimethylsilyl)trifluoroacetamide (BSTFA), trimethylsilyl chloride (TMSCl), N,O-bis(trimethylsilyl)acetamide (BSA), tert-butyldimethylsilyl trifluoromethanesulfonate (TBSOTf) and tert-butyldimethylsilyl chloride (TBSCl).

10. The process of claim 8, wherein the silylating is conducted in the presence of a solvent, or in the absence of a solvent and the silylating agent acts as a solvent.

11. The process of claim 1, wherein the salt forming agent is selected from the group consisting of D- or L-malic acid, camphorsulfonic acid, tartaric acid, trifluoroacetic acid, benzoic acid (BzOH), acetic acid (AcOH), methanesulfonic acid (MsOH), HCl, HBr, $H_2SO_4$, HF, and $3HF \cdot Et_3N$.

12. The process of claim 1, wherein the compound of formula (I) is sunitinib with the following formula:

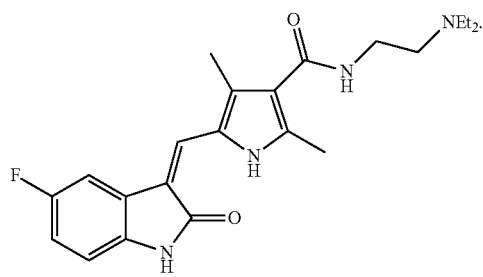

13. The process of claim 1 wherein the compound of formula (I) is sunitinib and the process further comprises steps of:
i) quenching crude sunitinib obtained from the reacting step (a) with an aqueous base to give a wet cake;
ii) reslurrying the wet cake with an alcohol and filtering; and
iii) drying the filter cake to give substantially pure sunitinib.

14. The process of claim 1 wherein the salt of the substituted 3-((pyrrol-2-yl)methylene)-2-pyrrolone of the formula (I) is sunitinib L-malate, and the step b) is conducted to obtain a crude sunitinib L-malate in solid form, the process further comprises steps of:
i) pre-heating dimethylsulfoxide (DMSO) to about 45° C.;
ii) adding the crude sunitinib L-malate in solid form to the pre-heated dimethylsulfoxide (DMSO);
iii) adding methyl isobutyl ketone (MIBK) into the mixture of ii); and
iv) cooling and filtering the mixture of 11i) to provide substantially pure sunitinib L-malate.

15. The process of claim 1, wherein the solvent is selected from the groups consisting of nitriles, haloalkanes, aromatics, esters, ethers, amides, sulfoxides, ketones, alkanes, and mixtures thereof.

16. The process of claim 1, wherein the solvent is selected from the group consisting of 1,2-dichloroethane (DCE), dichloromethane (DCM), chloroform ($CHCl_3$), toluene (PhMe), N,N-dimethylformamide (DMF), N,N-dimethylacetamide (DMAC), N-methyl-2-pyrrolidone (NMP), dimethylsulfoxide (DMSO), ethyl acetate (EtOAc), acetonitrile (MeCN), n-heptane, 1,4-dioxane, acetone, methyl isobutyl ketone (MIBK), and tetrahydrofuran (THF), and mixtures thereof.

17. The process of claim 1, wherein the reacting step a) is conducted at a temperature between 0° C. and 200° C.

18. The process of claim 1 further comprising reacting a compound of formula (VI):

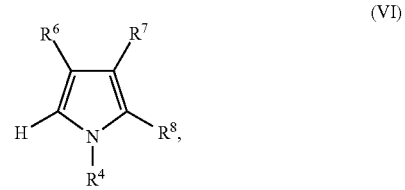

wherein $R^6$ and $R^7$ and $R^8$ are defined as in claim 1, with a salt of formula (VII):

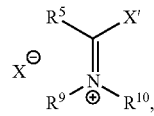
(VII)

wherein X is as defined in claim 1, and X' is Cl, Br, or triflate (OTf); $R^5$ is H or $C_1$-$C_8$ alkyl, $R^9$ and $R^{10}$ are independently $C_1$-$C_{12}$ alkyl, or in the alternative, $R^9$ and $R^{10}$ form a ring together, to prepare the compound of formula (V).

19. The process of claim 1 further comprising reacting the compound of formula (II):

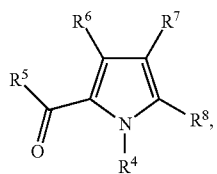
(II)

wherein $R^5$, $R^6$, $R^7$ and $R^8$ are defined as in claim 1, with a compound of formula (VIII) or an acid (HX) salt thereof:

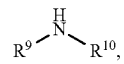
(VIII)

wherein $R^9$ and $R^{10}$ are independently $C_1$-$C_{12}$ alkyl, or in the alternative, $R^9$ and $R^{10}$ form a ring together, and X is defined as in claim 1, to obtain the compound of formula (V).

20. The process of claim 1 wherein the reaction between the compound of formula (III) and the compound of formula (V) in the reacting step a) is conducted in the absence of a Lewis acid or Brønsted acid catalyst.

21. The process of claim 1 wherein the reaction between the compound of formula (III) and the compound of formula (V) in the reacting step a) is conducted in a solvent.

* * * * *